US012122580B2

(12) United States Patent
Komann et al.

(10) Patent No.: US 12,122,580 B2
(45) Date of Patent: *Oct. 22, 2024

(54) HOLDING STRUCTURE FOR SIMULTANEOUSLY HOLDING A PLURALITY OF CONTAINERS FOR SUBSTANCES FOR PHARMACEUTICAL, MEDICAL OR COSMETIC APPLICATIONS, TRANSPORT UNIT AND TRANSPORT OR PACKAGING CONTAINER HAVING THE SAME

(71) Applicant: SCHOTT Pharma Schweiz AG, St. Gallen (CH)

(72) Inventors: Christian Komann, Speicher (CH); Arne Kloke, St. Gallen (CH); Anil Kumar Busimi, St. Gallen (CH)

(73) Assignee: SCHOTT Pharma Schweiz AG, St. Gallen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/357,982

(22) Filed: Jul. 24, 2023

(65) Prior Publication Data
US 2024/0025611 A1 Jan. 25, 2024

Related U.S. Application Data

(63) Continuation of application No. 16/685,430, filed on Nov. 15, 2019, now Pat. No. 11,794,974.

(30) Foreign Application Priority Data

Nov. 16, 2018 (DE) ..................... 10 2018 128 817.4

(51) Int. Cl.
*B65D 71/70* (2006.01)
*A61J 1/16* (2023.01)
(Continued)

(52) U.S. Cl.
CPC ............... *B65D 71/70* (2013.01); *A61J 1/16* (2013.01); *A61J 7/0069* (2013.01); *A61M 5/008* (2013.01);
(Continued)

(58) Field of Classification Search
CPC ........ B65D 71/70; B65D 25/108; B65D 1/36; A61J 1/16; A61J 1/165; A61J 7/0069; B01L 9/06; B01L 3/50855; A61M 5/008
(Continued)

(56) References Cited

U.S. PATENT DOCUMENTS 5,913,473 A 6/1999 Wang
9,403,619 B2 8/2016 Deutschle et al.
(Continued)

FOREIGN PATENT DOCUMENTS

CN 103359348 A 10/2013
DE 198 15 993 A1 10/1999
(Continued)

OTHER PUBLICATIONS

European Communication pursuant to Article 94(3) EPC dated Mar. 17, 2021 for European Patent Application No. 19 207 803.8 (6 page).

*Primary Examiner* — Rafael A Ortiz
(74) *Attorney, Agent, or Firm* — Taylor IP, P.C.

(57) ABSTRACT

A holding structure includes receptacles formed by peripherally formed side walls, an annular gap being formed between a side wall of a container or device and one of the peripherally formed side walls when containers or devices are received therein, the receptacles being compressed in a first direction and expanded in a second direction transversely thereto, with the result that the gap is widened to form a widened clearance for handling containers or devices which are received in the receptacles, the holding structure
(Continued)

further including an upper side, the peripherally formed side walls including an upper edge which forms a closed, smooth curve having at least one local maximum and at least one local minimum in a direction perpendicular to the upper side of the holding structure, the at least one local minimum being situated in a region of the widened clearance that is respectively assigned.

12 Claims, 29 Drawing Sheets

(51) Int. Cl.
    *A61J 7/00*     (2006.01)
    *A61M 5/00*     (2006.01)
    *B01L 3/00*     (2006.01)
    *B01L 9/06*     (2006.01)
    *B65D 1/36*     (2006.01)
    *B65D 25/10*     (2006.01)

(52) U.S. Cl.
    CPC ............ *B01L 3/50855* (2013.01); *B01L 9/06* (2013.01); *B65D 1/36* (2013.01); *B65D 25/108* (2013.01); *B01L 2200/021* (2013.01); *B01L 2200/025* (2013.01)

(58) Field of Classification Search
    USPC ..... 206/507, 528, 538, 562, 564, 534.1, 519
    See application file for complete search history.

(56) References Cited

U.S. PATENT DOCUMENTS

| | | |
|---|---|---|
| 10,610,322 B2 | 4/2020 | Escobar Fuertes |
| 2006/0016156 A1 | 1/2006 | Bush et al. |
| 2007/0172631 A1 | 7/2007 | Hugenholtz |
| 2009/0288977 A1 | 11/2009 | Vanderbush et al. |
| 2012/0118777 A1 | 5/2012 | Kakiuchi et al. |
| 2012/0181285 A1 | 7/2012 | Krauss et al. |
| 2014/0171829 A1 | 6/2014 | Holmes et al. |
| 2015/0166217 A1 | 6/2015 | Deutschle et al. |
| 2018/0208377 A1 * | 7/2018 | Kloke ................. B65B 3/003 |
| 2019/0142196 A1 * | 5/2019 | Barnum ................ B65D 71/70 |
| | | 206/459.5 |

FOREIGN PATENT DOCUMENTS

| | | |
|---|---|---|
| DE | 10 2009 027 454 A1 | 1/2011 |
| DE | 20 2016 107 209 U1 | 5/2018 |
| DE | 10 2017 101 398 A1 | 7/2018 |
| DE | 102018111491 A1 | 11/2019 |
| EP | 2 848 882 A1 | 5/2013 |
| WO | 2012/126582 A1 | 9/2012 |
| WO | 2014/130349 A1 | 8/2014 |
| WO | 2016111698 A1 | 7/2016 |
| WO | 2017/038878 A1 | 3/2017 |
| WO | 2017139385 A1 | 8/2017 |
| WO | WO-2017132554 A1 * | 8/2017 ............ A61M 5/008 |

* cited by examiner

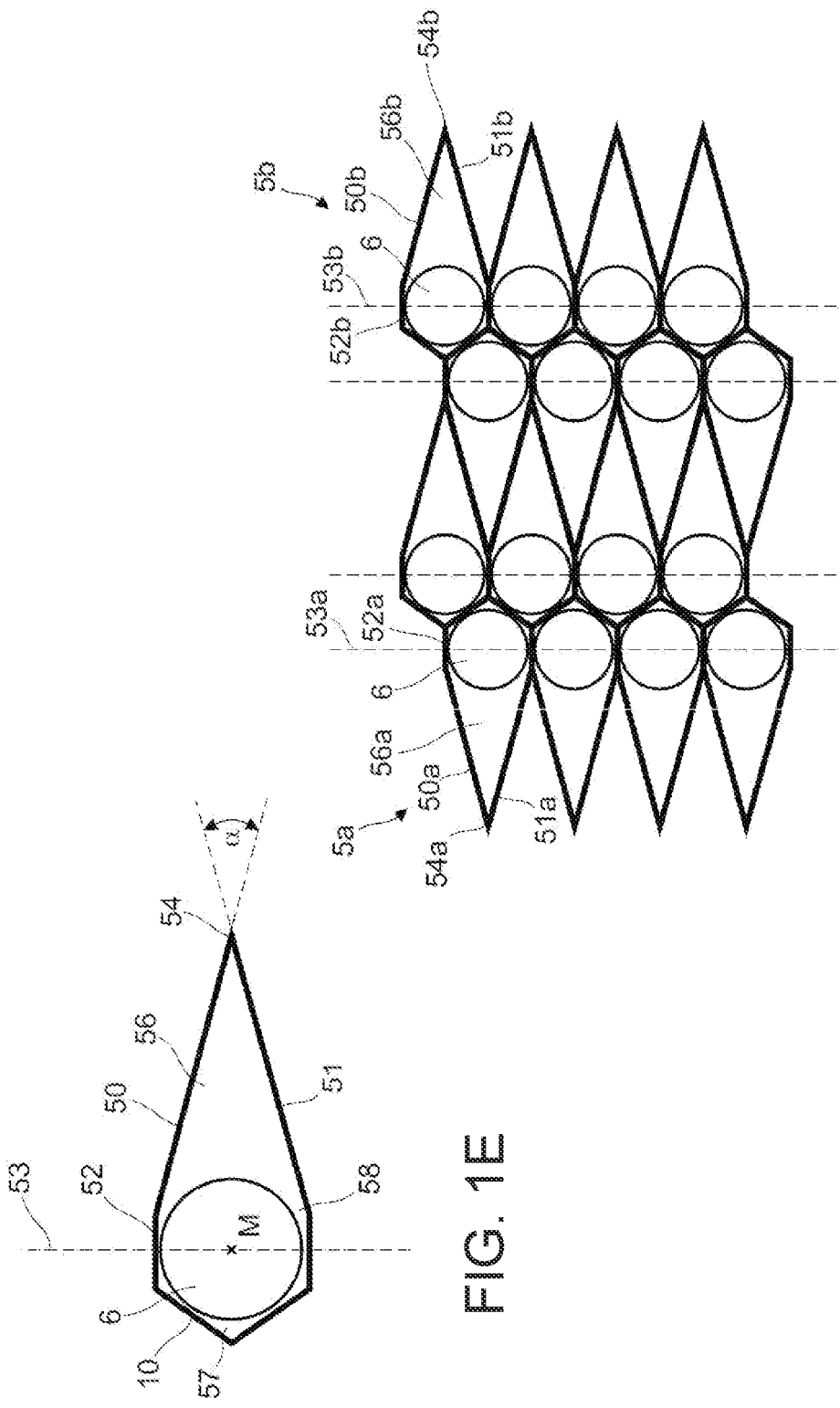

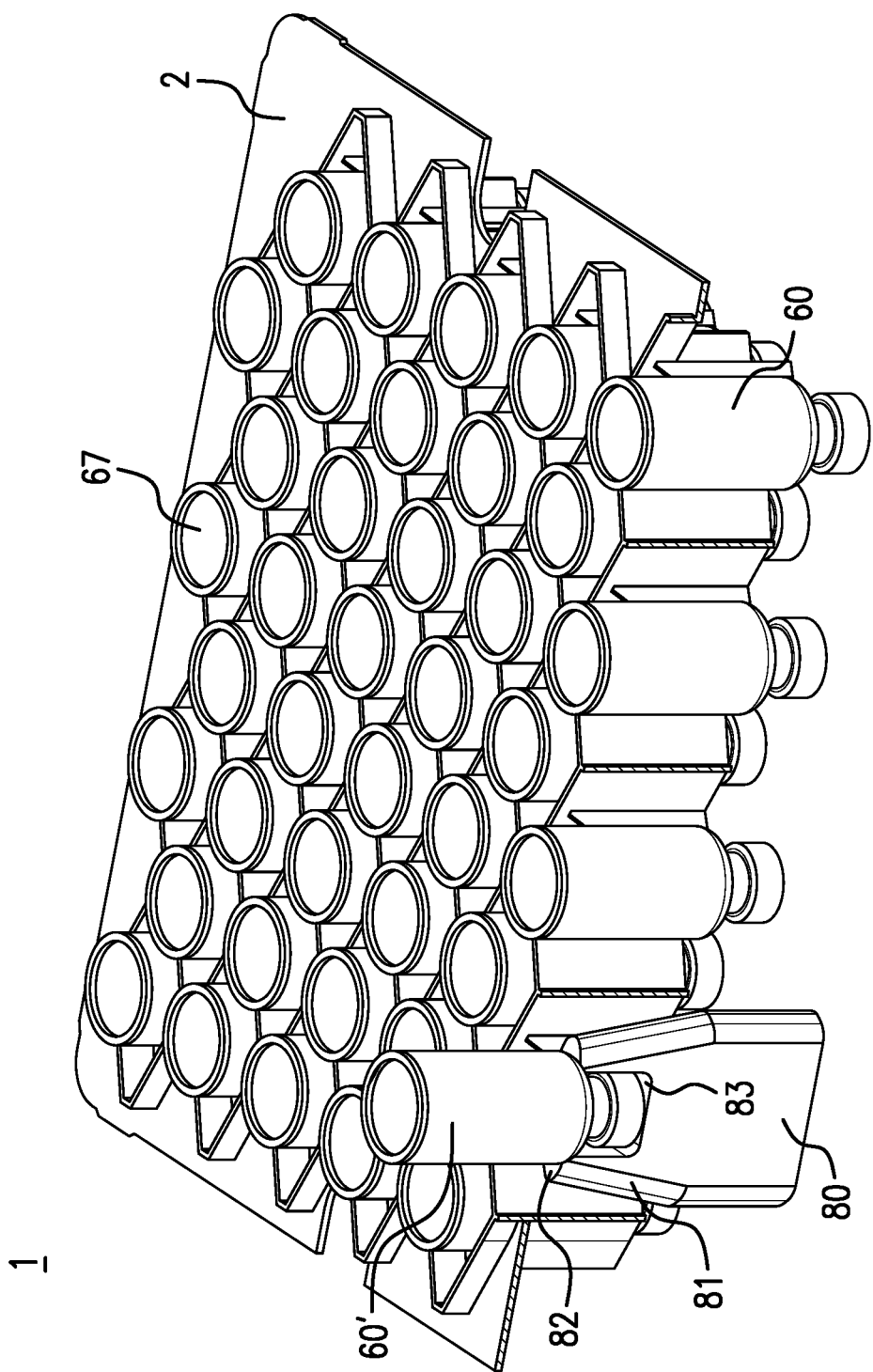

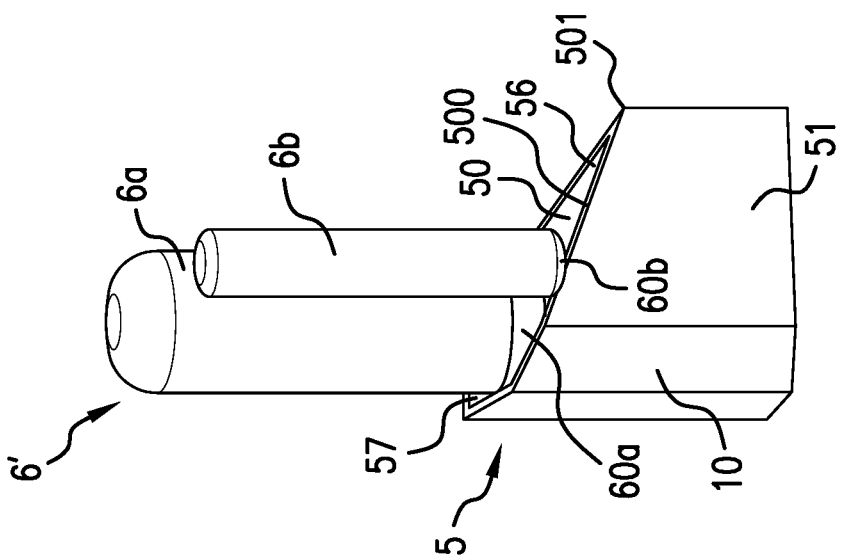
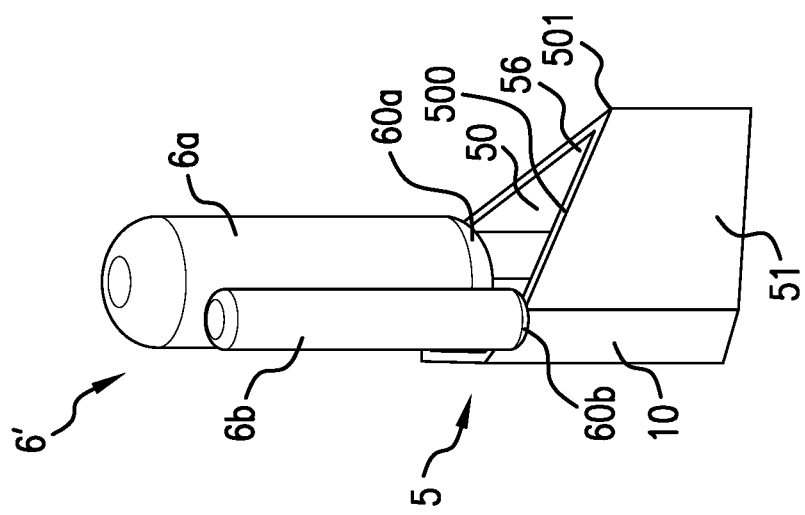
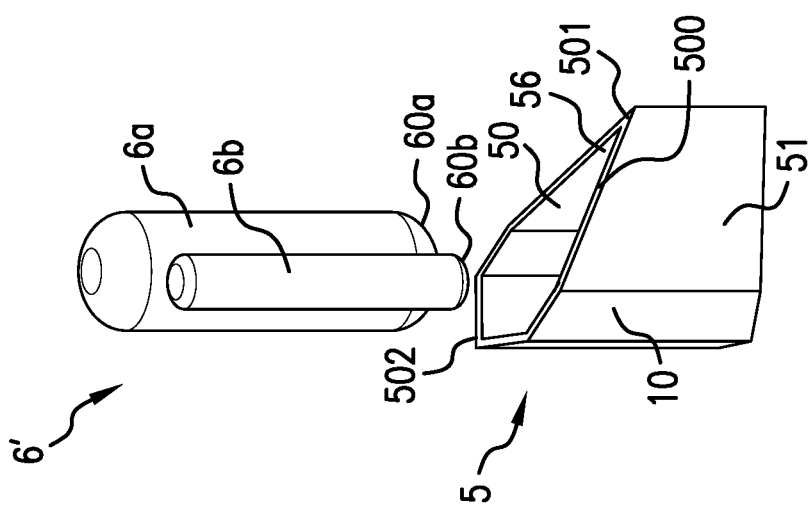

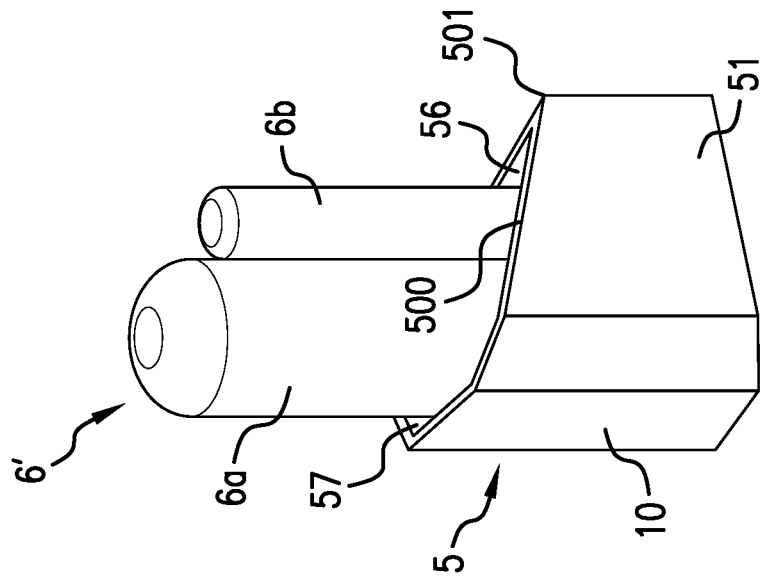
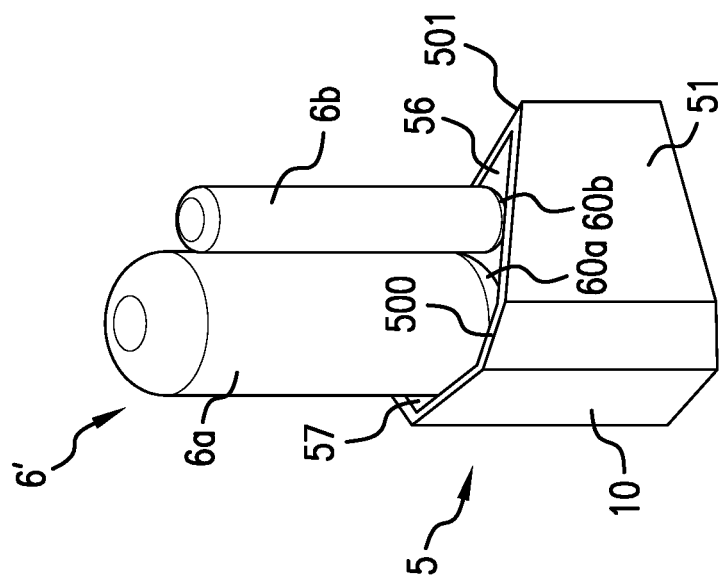

HOLDING STRUCTURE FOR SIMULTANEOUSLY HOLDING A PLURALITY OF CONTAINERS FOR SUBSTANCES FOR PHARMACEUTICAL, MEDICAL OR COSMETIC APPLICATIONS, TRANSPORT UNIT AND TRANSPORT OR PACKAGING CONTAINER HAVING THE SAME

CROSS REFERENCE TO RELATED APPLICATIONS

This is a continuation of U.S. patent application Ser. No. 16/685,430, entitled "HOLDING STRUCTURE FOR SIMULTANEOUSLY HOLDING A PLURALITY OF CONTAINERS FOR SUBSTANCES FOR PHARMACEUTICAL, MEDICAL OR COSMETIC APPLICATIONS, TRANSPORT UNIT AND TRANSPORT OR PACKAGING CONTAINER HAVING THE SAME", filed Nov. 15, 2019, which is incorporated herein by reference. U.S. patent application Ser. No. 16/685,430 claims priority to German patent application no. 10 2018 128 817.4, filed Nov. 16, 2018, which is incorporated herein by reference.

BACKGROUND OF THE INVENTION

1. Field of the Invention

The present invention relates generally to the treatment of containers for substances for pharmaceutical, medical or cosmetic applications, and relates in particular to a holding structure for simultaneously holding a plurality of containers for substances for pharmaceutical, medical or cosmetic applications, such as, for example, vials, ampoules or carpoules, or of more complex assemblies having such containers.

2. Description of the Related Art

Medicament containers, such as, for example, vials, ampoules or carpoules, are widely used as containers for storing medical, pharmaceutical or cosmetic preparations for administration in liquid form, in particular in pre-dosed quantities. These medicament containers generally have a cylindrical shape, can be produced from plastics or from glass and can be obtained in a cost-effective manner in large numbers. In this respect, the containers are increasingly being delivered in holding structures in a predetermined geometric arrangement to a pharmaceutical manufacturer or to a subsequent processing operation and are further processed while the containers are held or received in the holding structure. For this purpose, cost-effective and durable holding structures are required in which the containers are held or received in an arrangement which takes up the least possible space.

CN 103359348-A discloses a holding structure in the form of a trough-shaped holding tray, having a bottom on which there are provided a plurality of vertical positioning pegs between which the containers can be received without mutual contact. The holding structure is formed from a plastic by injection molding. The vertical positioning pegs simultaneously act as guide portions for inserting the containers into the receptacles formed by the positioning pegs. However, the containers are held with comparatively large play. The achievable packing density of the containers is relatively small.

WO 2012/126582 A1 discloses a further holding structure for syringe bodies, having a plate-shaped carrier on which there are formed a plurality of cylindrical receptacles having peripherally formed side walls. The syringe bodies rest by way of their holding flanges on the upper ends of the cylindrical receptacles. In order to stiffen the carrier, the cylindrical receptacles are connected to one another via connecting webs on the lower side of the carrier. The distance between the cylindrical receptacles is comparatively large, with the result that the packing density which can be achieved by the holding structure is not optimal.

WO 2014/130349 discloses a comparable holding structure.

WO 2017/038878 A1 discloses a further holding structure, having a plate-shaped carrier on which there are formed a plurality of cylindrical receptacles having peripherally formed side walls. The cylindrical receptacles are arranged at a comparatively small distance from one another, which, however, makes it necessary to produce two side walls at a relatively small distance from one another. During production by plastic injection molding, this necessitates very thin-walled, easily breakable rib-like contours which are difficult to cool. This leads in turn, in the design of the mold, to a very complex and thus also expensive mold. Moreover, such a design can also have a negative effect on the service life of the mold used for the injection molding. Since these delicate structures can be cooled only with very great effort, if at all, during injection molding, the design also has a negative impact on the cycle time of the production process, which leads to higher unit costs.

German Utility Model DE 20 2016 107 209 discloses a further holding structure of the aforementioned type in which inner receptacles of the holding structure are formed by axially extending positioning cylinders and separating webs which connect the positioning cylinders to one another. Although this arrangement allows a higher packing density of the containers, the production of the holding structure by plastic injection molding is comparatively complicated.

The not yet laid-open German Patent Application DE 10 2017 101 398.9 discloses a further holding structure in which the receptacles are formed by comparatively thin separating and connecting webs, which makes the production of the holding structure by plastic injection molding comparatively complicated.

German Patent Application DE 10 2018 111 491.5 "Holding structure for simultaneously holding a plurality of containers for substances for pharmaceutical, medical or cosmetic applications, transport unit and transport or packaging container having the same" discloses a holding structure for simultaneously holding a plurality of containers for substances for pharmaceutical, medical or cosmetic applications, having a plurality of receptacles for receiving the containers, wherein the receptacles are arranged in a regular arrangement, and, when viewed in a plan view, the receptacles are of polygonal design. Here, the receptacles are formed by side walls and in each case peripherally, wherein a side wall is formed as a common separating wall between every pair of directly adjacent receptacles of the plurality of receptacles.

For a wide variety of reasons, use is usually made, according to the prior art, of holding structures in which the receptacles are formed by peripheral side walls. For holding containers having a cylindrical basic body, the receptacles here always have either a circular basic shape or the basic shape of a quadrangle, namely a square or rectangle, or of a hexagon, as disclosed in DE 198 15 993 A1.

FIG. 1A summarizes the geometry of holding containers 102 having a cylindrical basic body in hexagonally formed receptacles 101 of a holding structure 100 according to the prior art. In each of the six corners of the receptacles there in each case converge two adjacent side walls 105, 106 at an angle θ=60°, as indicated by the dashed lines. Here, only a comparatively narrow gap 104 remains between the cylindrical side wall of the containers 102 and the side walls 105, 106 of the receptacles 101, where the width of the gap is generally minimized for reasons of optimizing the packing density of the holding structure 100 and is generally determined by the length of guide ribs on the side walls 105, 106 which serve for inserting and positioning the containers 102 in the receptacles 101.

In the case of receptacles 101 having a quadrangular or hexagonal basic shape, the maximum width of this gap 104 is formed by the height of a triangle which substantially corresponds to the length of the guide ribs on the side walls 105, 106. In the case of receptacles 101 having a circular basic shape, the width of this gap 104 along the outer circumference of the container 102 received is constant and is determined by the length of the guide ribs on the side walls 105, 106.

This means that, for the access to containers and the handling (for example the lifting or removal) of containers which are received in the receptacles of a holding structure of the aforementioned type, particular measures have to be provided for the engagement of auxiliary tools, which frequently reduce the stability of the holding structures.

What is common to holding structures having hexagonally formed receptacles is that directly adjacent side walls 105, 106, which converge in a corner region of the receptacles 102, enclose an obtuse angle Θ=120°, as is indicated in FIG. 1A by the dashed lines. In the case of octagonally formed receptacles 102, directly adjacent side walls 105, 106 enclose an angle Θ=135°. In the case of square or rectangular receptacles, directly adjacent side walls 105, 106 enclose, by contrast, a right angle (Θ=90°).

Thus, for example, DE 10 2009 027 454 A1 discloses a holding structure having a plate-shaped carrier plate on the lower side of which there is formed a plurality of cylindrical receptacles which, starting with the carrier plate, are first formed by peripheral side walls on the lower ends of which, however, longitudinal slots are formed on two diametrically opposite sides and allow the engagement of a strip-shaped tool for lifting a row of containers in the receptacles. Therefore, the side walls of the receptacles cannot be formed peripherally on the lower ends, which reduces the mechanical stability of the receptacles and can lead in particular to the receptacles being spread apart when forces acting perpendicularly to the receptacles are applied to the containers.

There is thus further need for improvement in the production of holding structures of the aforementioned type.

SUMMARY OF THE INVENTION

Exemplary embodiments disclosed herein provide an improved holding structure for simultaneously holding a plurality of containers for substances for pharmaceutical, medical or cosmetic applications that can be produced in a simple and cost-effective manner and allows an advantageously high stiffness and a high packing density of the containers. At the same time, it is possible to insert the containers into the receptacles of the holding structure and also to remove them again therefrom in a simple and reliable manner. Further aspects of the present invention relate to a transport unit or transport or packaging container and to a sterile packaging structure having such a holding structure.

In some exemplary embodiments provided according to the present invention, a device for simultaneously holding a plurality of containers for substances for pharmaceutical, medical or cosmetic applications or of devices having such containers is provided. The device includes: a holding structure comprising a plurality of receptacles configured to each receive a respective container, the receptacles being arranged in a regular arrangement and formed by peripherally formed side walls. The receptacles are configured to tailor to an outer contour of the containers or devices in such a way that an annular gap is formed between a side wall of a container or device and a side wall of a respective receptacle when the containers or devices are received in the receptacles. The receptacles, as viewed in a plan view, starting from an imaginary basic shape that is point-symmetrical or mirror-symmetrical, are compressed in a first direction and expanded in a second direction transversely to the first direction, with the result that the gap in at least one region of the receptacles is widened to form a widened clearance for handling containers or devices which are received in the receptacles.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIGS. 1C to 1E illustrate examples of basic shapes of receptacles of a holding structure provided according to exemplary embodiments of the present invention;

FIG. 1F illustrates a detail of a holding structure provided according to an exemplary embodiment of the present invention in a schematic plan view;

FIG. 8C illustrates the supporting of a carpoule in a combination according to FIG. 8A in a perspective partial section in a lifted state of the carpoule;

FIGS. 9A to 9E illustrate sequentially different phases during the insertion of a container having a lateral extension into a receptacle of a holding structure according to a further exemplary embodiment of the present invention;

Corresponding reference characters indicate corresponding parts throughout the several views. The exemplification set out herein illustrate embodiments of the invention and such exemplifications are not to be construed as limiting the scope of the invention in any manner.

DETAILED DESCRIPTION OF THE INVENTION

Figure 1B:
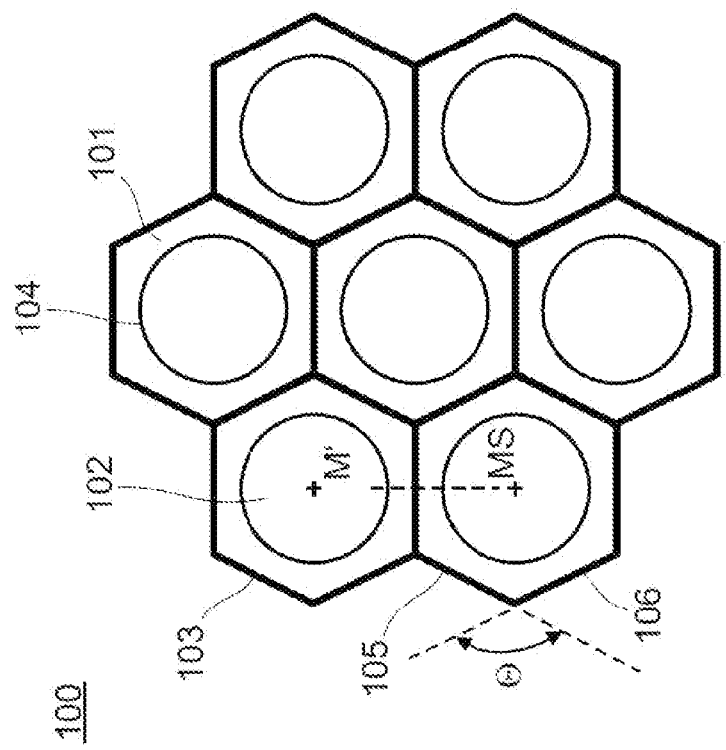
FIG. 1B illustrates a detail of a holding structure provided according to an exemplary embodiment of the present invention in a schematic plan view.

According to the present invention, a holding structure is provided for simultaneously holding a plurality of containers for substances for pharmaceutical, medical or cosmetic applications or of devices which have such containers, having a plurality of receptacles for receiving the containers or devices, wherein the receptacles are arranged in a regular arrangement and wherein the receptacles are formed by peripherally formed side walls. Here, the receptacles are tailored to an outer contour of the containers or devices in such a way that an annular gap is formed between side walls of the containers or devices and the peripherally formed side walls of the receptacles when the containers or devices are received in the receptacles. For this purpose, the aforementioned gap can be precisely predetermined in particular by guide and positioning ribs which extend radially inwardly into the receptacles. Here, the width of this annular gap could well be infinitesimal in certain portions, for example at a few punctiform regions.

According to the present invention, as viewed in a plan view, the receptacles, starting from an imaginary point-symmetrical or mirror-symmetrical basic shape, are compressed in a first direction and expanded in a second direction transversely to the first direction, with the result that the gap in at least one region of the receptacles is widened to form a widened clearance, for handling containers or devices which are received in the receptacles. The at least one widened clearance can considerably facilitate handling of containers or devices which are received in the receptacles, because the containers or devices received in the receptacles are considerably more easily accessible with the aid of tools and the like.

The imaginary point-symmetrical or mirror-symmetrical basic shape can in particular be a circle or a regular n-gon (where n is greater than or equal to 4). Here, when viewed in a plan view, the shape of the receptacles can be non-point-symmetrical. Conceivable in principle, however, are also point-symmetrical basic shapes of the receptacles, in particular receptacles which are non-point-symmetrical but mirror-symmetrical.

Whereas a point reflection, can always be found for the geometric figure (for example regular n-gon or circle) formed in each case by a customary receptacle, which point reflection this figure projects on itself, such a center of symmetry cannot necessarily be found for the receptacles provided according to the present invention.

The aforementioned gap expediently has a constant gap width between a container or device received in a receptacle and the side wall of the receptacle and is expediently precisely predetermined by guide and positioning ribs, while the gap width is very much larger only in the one edge region or in the two edge regions having the widened clearance, in order to allow access to the containers or devices by tools or the like. Here, in the region of the respective widened clearance, the geometry of the receptacle differs considerably from the geometry in all other regions of the receptacle. Whereas the receptacles have, for example, predominantly a radially symmetrical or point-symmetrical or else mirror-symmetrical basic shape, for example a circular, square or hexagonal basic shape, the shape of the respective widened clearance differs considerably from the geometry of this basic shape in all other portions of the receptacle.

According to the present invention, this geometry of the receptacles makes it possible to realize a very high area use index (packing density) in conjunction with an optimum accessibility of the containers or devices, which are received in the receptacles, for their handling. By virtue of the basic shape of the receptacles that differs from a circular basic shape or from the basic shape of a regular polygon, there is, according to the present invention, sufficient space available for receiving even large asymmetrically formed containers (for example subassemblies for microinjectors or the like), the handling of which is facilitated according to the present invention by virtue of the available widened clearances.

The widened clearances furthermore make available additional flow paths for the exchange of gases in transport and packaging containers which receive the holding structure with the containers or devices held thereon, for example when the interior of a transport and packaging container, the holding structure and the internal volumes of the containers or devices held thereon are intended to be sterilized by the inflow of a gas into the transport and packaging container.

Here, the receptacles are expediently compressed in the first direction and expanded in the second direction transversely to the first direction in such a way that a width of the receptacles in the first direction is less than the width of the imaginary basic shape in the first direction and such that a width of the receptacles in the second direction transversely to the first direction is greater than the width of the imaginary basic shape in the second direction. Here, the compression and expansion factors which determine the basic shape of the receptacles can in principle be identical or else different.

In some embodiments, the receptacles are expediently compressed in the first direction and expanded in the second direction transversely to the first direction in such a way that a width of the receptacles in the first direction is less than the width of the imaginary basic shape in the second direction and such that a width of the receptacles in the second direction transversely to the first direction is greater than the width of the imaginary basic shape in the second direction. Here, the compression and expansion factors which determine the basic shape of the receptacles can in principle be identical or else different.

In some embodiments, the receptacles have a hexagonal basic shape or they are derived from a hexagonal basic shape, wherein the width of the receptacles in the second direction is greater by at least 30%, such as by at least 22% or by at least 17%, than the width of the receptacles in the first direction. According to the present invention, the geometry of the receptacles differs markedly from the geometry of a regular hexagon for which the ratio between minimum width and maximum width is approximately 1:1.16.

In some embodiments, a width of the gap close to apexes of the receptacles which are situated opposite to one another along the first direction is infinitesimal or is less than a width of the gap close to corner or edge regions of the receptacles which are situated opposite to one another along the second direction, wherein the last-mentioned width can be determined in a simple manner through the choice of the aforementioned expansion factor of the receptacles.

In some embodiments, the receptacles are arranged in a distributed manner in a hexagonal regular arrangement, wherein the widened clearances between the containers or devices are asymmetrically assigned to the surrounding containers or devices. Because the clearances differ from the normal geometry in all other portions of the clearances, it is possible according to the present invention to provide widened clearances in order to allow access to the containers or devices, which are received in the receptacles, for their handling.

In some embodiments, the widened clearance is formed by a corner region which is formed by two side walls which, as viewed in plan view, converge to a point or to a short connecting web at a convergence angle in order to form the widened clearance, wherein the following holds for the convergence angle: $0°<\alpha<110°$, such as $0°<\alpha<45°$ or $0°<\alpha<30°$.

In other words: in the region of the respective widened clearance, the apex angle of the widened clearance is less than the apex angle which corresponds to the geometry of an equilateral hexagon ($\alpha=120°$), an octagon ($\alpha=135°$) or dodecagon ($\alpha=160°$), which, according to the prior art, are used as basic shape for receptacles of holding structures. The aforementioned gap between a container or device received in a receptacle and the side wall of the associated receptacle is thus stretched or expanded radially outwards in one region or in two regions of the receptacle in order to form a widened clearance which considerably simplifies handling of a container or device received in the receptacle, in particular by inserting a tool, for example a gripping tool or tool for lifting the container or device, into the thus provided widened clearance.

The geometry of the receptacle can expediently correspond, in all other regions, with the exception of the one widened clearance or of the two widened clearances, to a simple geometry, for example corresponding to a cylindrical basic shape, to a point-symmetrical geometry, to a mirror-symmetrical symmetry or to the symmetry of an equilateral polygon (in particular hexagon or octagon), whereas the geometry of the respective widened clearance, on account of the aforementioned expansion or stretching radially outwards, differs considerably from this geometry in all other regions.

In some embodiments, the converging side walls of the receptacles can converge in a linear corner region which extends in each case in the longitudinal direction of the receptacles and is arranged in a corner region of the respective receptacles; or the converging side walls can form, with the short connecting web, in each case a linear corner region which extends in each case in the longitudinal direction of the receptacles and is arranged in a corner region of the respective receptacles. This simple modification of the geometry of the receptacles makes it possible in a simple manner to achieve a widened clearance for handling the containers or devices received in the receptacles. The holding structure can nevertheless be produced cost-effectively and with comparatively simply designed molding tools, wherein an advantageously high packing density can be achieved at the same time.

In some embodiments, the receptacles can directly adjoin one another, wherein a side wall is formed as a common separating wall between each pair of directly adjacent receptacles of the plurality of receptacles, thus allowing an optimum packing density. By virtue of the commonly used separating wall, delicate, double-walled structures can be effectively avoided, which considerably simplifies the production by injection molding from a plastic. Thin-walled, easy breakable rib-like contours which are difficult to cool in the mold design can thus be avoided according to the present invention, which results in a longer service life of the mold. Furthermore, the cycle time of the production process can be significantly shortened and unit costs can be reduced.

The separating walls can be formed to be in particular relatively thin-walled, and a high intrinsic stiffness of the holding structure can nevertheless be realized. This allows a relatively low weight of the holding structure in combination with reduced use of material and low production costs.

At the same time, a very high intrinsic stiffness of the holding structure can be achieved because all the side walls are directly connected to one another by corner regions of the receptacles and together form a highly symmetrical hollow honeycomb structure, formed by the side walls which project perpendicularly from a plate-shaped upper side of the holding structure.

A common separating wall is to be understood as meaning within the context of the present invention in particular that the separating walls, as viewed in a cross section, are in each case formed in one piece and without substantial breaches. Here, the height of the respective common separating wall corresponds substantially to the axial length of the two directly adjacent receptacles, with the result that the respective common separating wall is formed, such as over at least 80% of this height, from a solid material.

In some embodiments, the side walls of the receptacles are in each case formed as planar, flat separating walls, wherein the side walls of directly adjacent receptacles converge in a connecting region which extends in each case in the longitudinal direction of the receptacles and is arranged in a corner region of the respective receptacles. The result is highly symmetrically formed connecting regions which, for example in the case of a hexagonal arrangement of the receptacles, when viewed in plan view, are star-shaped. This allows a highly symmetrical dissipation of forces, which results in an advantageously high intrinsic stiffness of the holding structure.

In some embodiments, the receptacles are in each case formed mirror-symmetrically with respect to an axis of symmetry, as viewed in plan view, wherein the at least one widened clearance is formed in a direction perpendicular to the axis of symmetry, and a small clearance having a considerably smaller opening width between the side walls of the receptacle and a container or device received therein is formed in the direction of extension of the axis of symmetry.

In some embodiments, as viewed in plan view, two apex points of side walls of the receptacles lie on the aforementioned axis of symmetry; or the aforementioned axis of symmetry intersects, as viewed in plan view, a flattened-off or symmetrically concavely curved side wall at a right angle. Here, the central portion of the receptacles has a geometry with a narrow edge gap between received container or device and side wall of the receptacle, which edge gap is expediently defined by guide and positioning ribs and has a constant gap width. At the same time, here, the geometry of the at least one widened clearance differs considerably from this geometry, with the result that, even with a high packing density, very good accessibility to the containers or devices by tools or the like for their handling can be achieved.

In some embodiments, as viewed in plan view, the converging side walls are in each case concavely curved in the form of an arc. The converging side walls thus meet in the corner region or into the short connecting web of the respective widened clearance at a negligible convergence angle ($\alpha=0°$), that is to say parallel to one another. Here, the length of the connecting web is considerably less than the opening width of the portion in which the container or the device is received.

In some embodiments, the receptacles have in each case two widened clearances for handling which are formed on mutually opposite corner regions or short connecting webs of the converging side walls. The receptacles are thus in each case formed mirror-symmetrically with respect to a center line. Therefore, a container or device received in a receptacle can, for its handling, be handled from the two clearances by a tool, for example by the gripping arms of a tool which in each case engage in one of the widened clearances and act laterally on the container or the device contained in the receptacle.

In some embodiments, the receptacles are of identical basic shape and they have in each case a widened clearance for handling which converges to a corner region or short connecting web and is formed by the converging side walls, wherein the receptacles are in each case arranged offset to one another along rows and columns extending perpendicularly to said rows, and wherein in each case receptacles which are directly adjacent to one another along the columns or rows are arranged in mirror-image fashion with respect to the column or row. In other words, the receptacles are in each case expanded or stretched in an alternating manner in opposite directions and are combined, in each case in an opposite orientation, to form a holding structure. Particularly in the case of receptacles having only one widened clearance which is expanded or stretched laterally or radially away from a central receptacle for receiving a container or device, it is thus possible according to the present invention to achieve a very high packing density with improved access to the containers or devices, which are received in the receptacles, for their handling.

In some embodiments, as viewed in plan view, the receptacles in each case have a hexagonal basic shape having, as viewed in plan view, two flat connecting webs which are noticeably shorter than the converging side walls. Here, the connecting webs of directly adjacent receptacles can also form a common separating wall used by both receptacles, which allows an even higher packing density. Here, the connecting webs can at the same time be aligned with the aforementioned axes of symmetry or center lines of the central receptacles in which the containers or devices are received. This arrangement simultaneously allows a high packing density and a very high intrinsic stiffness of the holding structure.

In some embodiments, the holding structure furthermore has a plate-shaped carrier which forms an upper side of the holding structure, wherein the side walls and receptacles project perpendicularly from the plate-shaped carrier. This further increases the intrinsic stiffness of the holding structure.

In some embodiments, an upper edge of the peripheral side walls forms a closed, smooth curve which has at least one local maximum and at least one local minimum in a direction perpendicular to the upper side of the holding structure, wherein the respective local minimum is situated in the region of a respectively assigned widened clearance. At the upper edge of the peripheral side walls there is thus formed a type of slide or inclined ramp which allows an angular orientation of containers or devices having an asymmetrical basic shape. Such containers or devices which are wider in a first direction than in a direction perpendicular thereto are, during insertion into the receptacles, guided automatically vertically from above and rotated in such a way that the first direction in which the containers or devices are wider is automatically oriented parallel to the direction of the receptacles in which the receptacles are wider. This makes possible an automatic angle of rotation orientation of the containers or devices.

In some embodiments, upper ends of the side walls which face an upper side of the holding structure have a profile which is curved concavely in the form of an arc, thus being funnel-shaped, which facilitates the insertion of the containers or devices from vertically above the holding structure into the receptacles. Here, in particular, the upper ends of the side wall do not project at any point from the upper side of the holding structure. This facilitates a space-saving stacking of the holding structures vertically above one another, since an undesired jamming of the upper ends of the side walls is avoided.

In some embodiments, guide ribs are formed on the side walls and extend in the longitudinal direction of the receptacles and assist a threading or insertion of the containers or devices into the upper ends of the receptacles. Here, insertion bevels can be formed on the upper ends of the guide ribs and are inclined relative to the guide ribs in order to further facilitate the insertion of the containers or devices from the upper side of the holding structure into the receptacles.

In some embodiments, the guide ribs project inwardly into the receptacles in a direction towards the geometric center of the respective receptacle, with the result that the containers or devices can be positioned in a central receiving region at a distance from the side walls of the receptacles, wherein the at least one widened clearance projects laterally from this central receiving region. This optimized design of the guide ribs facilitates a low-wear insertion of the containers or devices. Here, the guide ribs expediently project inwardly into the receptacles in a direction towards the geometric center of the central receiving region of the respective receptacle.

In some embodiments, holding portions are provided on the lower ends of the receptacles in order to hold the containers in the receptacles and to limit the axial movability of the containers or devices in the receptacles towards the lower end of the receptacles. In principle, there suffices for this purpose a holding portion which is arranged at a suitable position on the lower end of a respective receptacle. In each case two holding portions lie diametrically opposite one another on the lower ends of the receptacles. In principle, however, the holding portions can also be designed to be peripheral or substantially peripheral, having one or more breaches along the circumference of the respective receptacle at its lower end.

According to the present invention, a very precise positioning and guidance of the containers or devices in the receptacles is possible in particular in the case of long, thin or slender containers where a very high packing density is achieved, because a glass-to-glass contact of containers with increasingly limited freedom of movement becomes more improbable.

The necessary guide length can also be reduced with a greatly reduced freedom of movement of the containers or devices in the receptacles. This is relevant for example in the case of long, thin or slender containers, such as, for example, carpoules or syringe cylinders, in particular with small sizes, because these can frequently be inserted into the receptacles only up to the lower half. On account of the very precise positioning and guidance, according to the present invention, of the containers or devices, it can nevertheless be reliably ensured that there is no glass-to-glass contact. Thus, according to the present invention, material can also be saved.

In some embodiments, the length of the receptacles is tailored to the length of the containers or devices in such a way that upper or lower ends of the containers or devices project from the receptacles and are thus freely accessible from above the holding structure. This can be used for a further processing or treatment of the containers or devices while they are received in the receptacles and held on the holding structure. For example, a holding structure (so-called nest) can be temporarily held in a holding frame of a process station, for instance at a pharmaceutical filling apparatus, while the substance is filled via the filling openings into the containers or devices held on the holding structure; or plugs or other suitable closure elements for closing the containers or devices are pressed into the ends of the containers or devices while the containers or devices are held on the holding structure; or the ends projecting from the receptacles can be used for gripping the containers or devices and for their removal from the receptacles.

In some exemplary embodiments provided according to the present invention, a transport unit for containers or devices having such containers is provided, consisting of a combination of the holding structure, as disclosed above, and a plurality of containers held thereon for substances for pharmaceutical, medical or cosmetic applications or of devices having such containers, wherein the containers or devices are received at least in certain portions in the receptacles of the holding structure and are held in an axially secured manner on the holding structure, as stated above. For this purpose, the holding structure can be formed in particular as a so-called nest in order to hold vials, carpoules or comparable pharmaceutical containers or else complex medical devices which contain such containers, such as, for example, subassemblies or microinjectors for self-medication. Because the receptacles have in each case at least one widened clearance, such as two widened clearances on diametrically opposite corner regions of the receptacles, pharmaceutical containers or complex medical devices can also be received whose outer contour is not circular, in particular has one or more radially projecting portions.

In some embodiments, the containers or devices are formed to be cylindrical, in particular as cylindrical carpoules or carpoules having a bypass, and these have an upper end with a narrowed neck portion and a shoulder portion which adjoins the narrowed neck portion and merges into a cylindrical side wall of the containers, wherein the opening width between holding projections on the lower ends of the receptacles is tailored to an outside diameter of the upper ends of the containers in such a way that the upper ends of the containers extend through the opening between the holding projections, and the shoulder portions of the containers are directly supported on the holding projections in order to limit the axial movability of the containers in the receptacles when the containers are received upside down in the receptacles.

In some embodiments, a transport or packaging container for a plurality of containers for substances for pharmaceutical, medical or cosmetic applications or a plurality of devices having such containers is provided, wherein the transport or packaging container is box-shaped, wherein a holding structure which, as stated above, is formed as a so-called nest, and is received in the box-shaped transport or packaging container together with the containers or devices held therein in order to hold the plurality of containers or devices in the transport or packaging container.

Here, the transport or packaging container can be closed or sealed in particular by a gas-permeable plastic film, in particular by a plastic film which is formed from a gas-permeable braid of plastic fibers and is in particular a Tyvek® film, in order to allow a sterilization of the containers or devices by the inflow of a gas through the gas-permeable plastic film.

In some embodiments, the transport or packaging container can be closed or sealed in particular by a gas-permeable plastic film, in particular by a plastic film which is formed from a gas-permeable braid of plastic fibers, such as a plastic film formed from high-density polyethylene fibers, and is in particular a Tyvek® film, in order to allow a sterilization of the containers or devices by the inflow of a gas through the gas-permeable plastic film.

For sterile transport and storage, there can further be provided a sterile packaging structure having at least one transport unit, as stated above, or having at least one transport or packaging container, as stated above, and having the containers or devices received therein, wherein the at least one transport unit or the at least one transport or packaging container is received in at least one sterile outer packaging bag and is packaged in a sterile manner with respect to the surroundings. Here, the at least one sterile outer packaging bag can have a gas-permeable portion which is formed in particular by a braid of plastic fibers, such as, for example, polypropylene fibers (PP).

Referring now to the drawings, FIG. 1B illustrates a detail of an exemplary embodiment of a holding structure 1 provided according to the present invention in a schematic plan view. The holding structure 1 has a plurality of receptacles 5 which are arranged in a regular arrangement (array) and serve for the reception of pharmaceutical containers, in particular of vials, carpoules or syringe bodies, or of more complexly designed assemblies having such pharmaceutical containers therein. According to the present invention, the receptacles 5 have the basic shape of an n-gon, where n is greater than or equal to four. A hexagonal basic shape (n=6) may be used, as illustrated in the exemplary embodiments according to FIGS. 1C to 1F, or a basic shape, as illustrated in the exemplary embodiment according to FIG. 1B, thus basically also a hexagonal basic shape, although two mutually directly opposite apexes 52 of side walls 50, as viewed in plan view, are concavely curved. Also conceivable in principle, however, is a square, rectangular or diamond-shaped basic shape of the receptacles, as illustrated for example in FIGS. 1G to 1J.

Corresponding to the basic shape of the receptacles 5, the latter are arranged directly adjoining one another in a regular arrangement. Thus, a hexagonal, honeycomb arrangement of the receptacles 5 can be seen in FIG. 1B. In principle, however, the receptacles 5 can, for example, be arranged offset to one another in rows and columns extending perpendicular thereto.

The opening width of the identically formed receptacles 5 is tailored to a maximum outside diameter or a maximum outer dimension of the containers to be received therein in such a way that the latter are received therein only with a comparatively small play and with the formation of a comparatively narrow gap between the containers 6 and the side walls 50-52 of the receptacles 5. Thus, in the exemplary embodiment according to FIG. 1B, a distance between mutually directly opposite apexes 52 is slightly larger than the diameter of the cylinder containers 6 received in the receptacles 5. This oversize is, as stated below, substantially predetermined by the distance by which guide and positioning ribs on the side walls 50 project into the receptacles 5.

The containers 6 may be nevertheless received over the largest part of their axial length in the receptacles 5 in order to prevent undesired tilting or wobbling of the containers in the receptacles during the transport of the holding structure 1. Here, the play of the containers 6 in the receptacles 5 is expediently set by guide ribs, as explained in more detail below.

The receptacles 5 are formed by side walls 50 which are formed peripherally, but this is not intended to exclude the possibility that, for example for weight reduction or material saving, breaches or cut-outs are formed at certain portions in the side walls 50. The side walls 50 may project at right angles from the plate-shaped upper side of the holding structure 1. To facilitate demolding of the holding structure 1 from a mold used for injection molding, the side walls can in principle also be inclined in a radially inwardly directed manner at a comparatively small angle of, for example, at most 1° or at most 2° with respect to a perpendicular to the upper side 2.

As illustrated in FIG. 1B, by virtue of the polygonal basic shape of the receptacles 5, a common separating wall is formed between in each case two directly adjacent receptacles 5 and serves simultaneously as a side wall 50 of the two receptacles 5 adjacent to one another. This means that the side walls 50 are formed in one piece and from a solid material, thus rectangular in cross section. This should expressly not exclude the possibility that slots or cut-outs could be provided on lower or upper ends of the side walls 50. Nevertheless, the side walls used in each case as a common separating wall are formed over at least 80% of their height from a solid material.

Figure 1A:
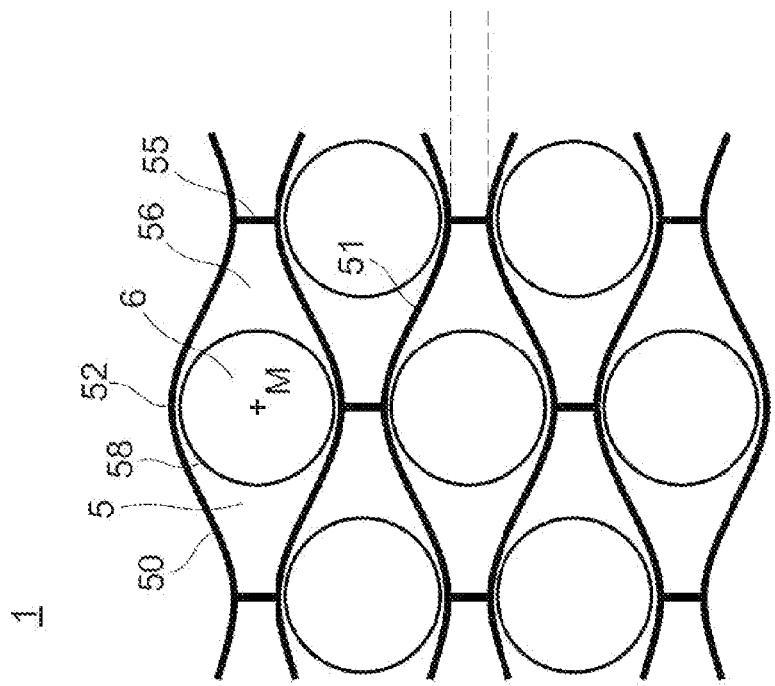
FIG. 1A illustrates a detail of a holding structure of the prior art in a schematic plan view.

The direct comparison of FIGS. 1A and 1B reveals the basic principle of the present invention, according to which the receptacles 5 are expanded at least in one direction perpendicular to the imaginary connecting line of two mutually directly opposite apexes 52, whereas the receptacles 5 are compressed in a direction perpendicular thereto, thus in the direction of this imaginary connecting line. In other words: the receptacles 5 are, as viewed in a plan view, starting from an imaginary point-symmetrical or mirror-symmetrical basic shape, compressed in a first direction, for example in FIG. 1C in the direction of the axis of symmetry 53, and expanded transversely to this first direction in a second direction, with the result that the gap in at least one region of the receptacles is widened to form a widened clearance 56 which facilitates handling of containers which are received in the receptacles 5.

In the exemplary embodiment of FIG. 1B, the receptacles 5, in the plane of the drawing, are expanded both in a direction to the left and in a direction to the right. There are thus created two widened clearances 56 whose dimensions are considerably greater than the corresponding small clearances 58 close to the two apexes 52. As is explained in more detail below with reference to FIGS. 8A to 8C, the widened clearances serve for access to the containers 6 received in the receptacles 5 by tools, such as, for example, grippers, tongs, lifting tools, plungers or the like, for handling and further treating the containers 6. As can be gathered from FIG. 1B, the dimensions of these widened clearances 56, in a direction perpendicular to the aforementioned imaginary connecting line, can indeed be of the order of magnitude of a diameter of the containers 6 received in the receptacles 5.

The exemplary embodiment of FIG. 1B is here based on the fact that the side walls 50 do not converge directly in a punctiform (as viewed in plan view) convergence region, but rather merge in each case into a relatively short connecting web 55 which extends parallel to the aforementioned imaginary connecting line. Here, the outer ends of the side walls 50 of a respective receptacle 5 intersect the connecting webs 55 substantially at a right angle, and thus extend parallel to one another at the point of intersection with the respective connecting web 55, as indicated by the two dashed lines in FIG. 1B. Within the sense of the present application, the two side walls 55 converge to a short connecting web at a convergence angle which is substantially infinitesimal in order to form two widened clearances 56 on opposite sides of the containers 6, which are received in the receptacles 5, for handling the containers.

According to FIG. 1B, as viewed in plan view, the receptacles 5 are formed mirror-symmetrically with respect to the aforementioned imaginary connecting line and also with respect to a line extending perpendicularly thereto. Of course, the ends of the two side walls 50 can also converge directly to a punctiform region, as with an infinitesimal length of the connecting webs 55, at a substantially infinitesimal convergence angle, that is to say with a substantially tangential approach to one another.

As can be readily gathered from FIGS. 1B to 1F, the dimension of the at least one widened clearance 56 is considerably greater than the width of the gap between the containers 6 received in the receptacles 5 and side walls 50-52 of the receptacles 5. Whereas the receptacles 5 are arranged in a distributed manner in a hexagonal rectangular arrangement, the widened clearances 56 between the containers 6 are asymmetrically assigned to the surrounding containers 6.

Figure 1D:
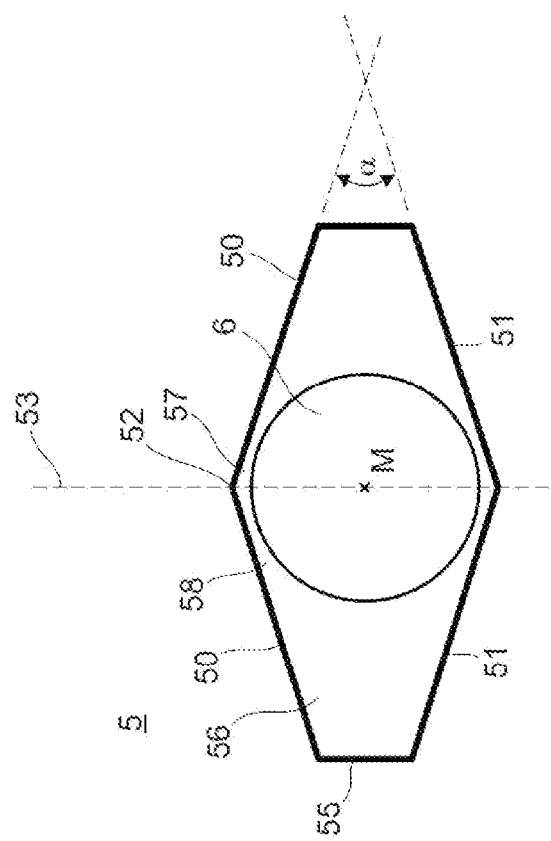
Figure 1C:
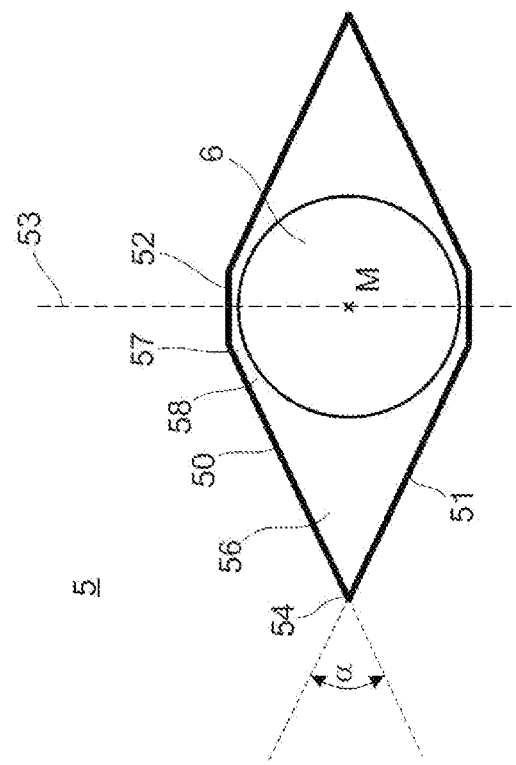

FIG. 1C illustrates a further possible hexagonal basic shape of a receptacle 5 according to the present invention, wherein in each case two side walls 50, 51 converge on two opposites sides of the axis of symmetry 53 in a punctiform (as viewed in plan view) corner region 54 at an acute angle α, for which the following holds: α<55°, such as α<45° or α<30°. The concrete size of the opening angle or convergence angle α is dependent on the desired dimension of the widened clearance 56 on both sides of the container 6 received in the receptacle 5. As can be gathered from FIG. 1C, the two mutually corresponding side walls 50 or 51 are connected to one another on both sides of the container 6 received in the receptacle 5 via a plate-shaped or, as viewed in plan view, curved connecting web 52. The container 6 is arranged in the receptacle 5 by guide and positioning ribs (not illustrated) with the formation of a comparatively narrow clearance 57, at a distance from the side walls 50-52, whereas the widened clearance 56 allows sufficient space for access to the container 6 by a suitably formed handling tool.

FIG. 1D illustrates a further possible hexagonal basic shape of a receptacle 5 provided according to the present invention, wherein in each case two side walls 50, 51 on two opposites sides of the axis of symmetry 53 converge in a comparatively short connecting web 55 which extends parallel to the axis of symmetry 53. If the two converging side walls 50, 51 are extended beyond the connecting web, they again enclose an acute angle α, for which the following holds: α<110°, such as α<45° or α<30°. As can be gathered from FIG. 1D, the two mutually corresponding side walls 50 or 51 in each case enclose an obtuse angle (180°−α) at the apex 52. As viewed in plan view, the two connecting webs can either extend rectilinearly, as illustrated in FIG. 1D, or else have a concavely curved profile.

FIG. 1E illustrates a further possible hexagonal basic shape of a receptacle 5 provided according to the present invention. Different from FIGS. 1B to 1D, the receptacle here is expanded only in a direction perpendicular to the aforementioned imaginary connecting line (corresponding to the axis 53 depicted in dashed line in FIG. 1E), whereas, on the opposite side of the axis 53, the basic shape corresponds to that of an equilateral hexagon. Whereas, as viewed in plan view, small clearances 57 are formed on the left side of the axis 53, the opening widths of which clearances are not sufficient for access to the container 6, the dimension of the widened clearance 56 on the opposite, right side of the axis 53 is considerably greater. This dimension can be even greater than the diameter of the container 6 received therein, as illustrated in FIG. 1E. The two converging side walls 50, 51 converge in a punctiform (as viewed in plan view) corner region 54 at an acute angle α, for which the following holds: α<110°, such as α<45° or α<30°. The concrete size of the opening angle or convergence angle ? is dependent on the desired dimension of the widened clearance 56.

If in general, for example, the basic shape of the receptacles 5 is based on the shape of a regular n-gon of side length a, the aforementioned convergence angle is at any rate less than the convergence angle of two side walls, which is 180°-360°/n, where (n≥4). In order to allow access by handling tools to the containers via the widened clearances 56, the convergence angle in the region of the widened clearance is expediently in each case considerably less than the convergence angle of a regular n-gon, which results in the aforementioned exemplary angle ranges, but is also dependent on the concrete application.

In order to form a holding structure with a receptacle 5 of the basic shape according to FIG. 1E, the receptacles are supplemented to form an arrangement, as illustrated in FIG. 1F. Expressed more simply, if each individual receptacle 5 is formed by a predetermined expansion in only one direction perpendicular to the axis 53 and with the formation of a widened clearance 56, the receptacles arranged offset to one another along columns (or rows) are expanded in alternating fashion in opposite directions. In other words, the receptacles 5 are in each case arranged offset to one another along rows and columns extending perpendicularly thereto, wherein in each case receptacles 5 which are arranged directly adjacent to one another along the columns or rows are arranged in mirror-image fashion with respect to the column or row. The containers 6 are thus offset along axes 53a and 53b and arranged directly adjoining one another with an alternatingly opposite orientation of the widened clearance 56.

According to the present invention, particularly the following advantages can be achieved by the diamond-shaped basic shape of the receptacles 5:

- free access from one or from two opposite sides to a container received in a receptacle for handling by a handling tool, for example a gripper;
- by comparison to conventional holding structures, an achievable packing density which is higher by up to 20%;
- a higher stiffness (upon exerting forces perpendicular to the holding structure, for instance when placing plugs into containers which are received in the receptacles of a holding structure, considerably less distortion of the holding structure occurs);
- more economical manufacture/shorter cycle times during the manufacture by injection molding/less expenditure on material;
- reduced mold complexity (smaller investment costs, higher service life);
- during production by injection molding from a plastic, the mold requires few, large cores only on one side of the mold, which makes possible very good cooling of the mold and of a holding structure produced therein;
- containers or more complexly designed units whose basic shape differs from the circular basic shape can also be received in the receptacles; for example, so-called bypass carpoules (with laterally projecting bypass) can be received.

For a nest for holding cylindrical carpoules, it has been illustrated that, given the same base area of the carrier, the packing density can be increased by up to 58% (increase in the number of carpoules which can be held on a holding structure with a predetermined base area from forty carpoules to sixty-three carpoules with a simultaneous reduction in the weight of the nest from about 160 g to 113 g and for a comparable stiffness of the nest).

FIGS. 1G to 1J illustrate some further exemplary basic shapes of quadrangular receptacles.

Figure 1H:
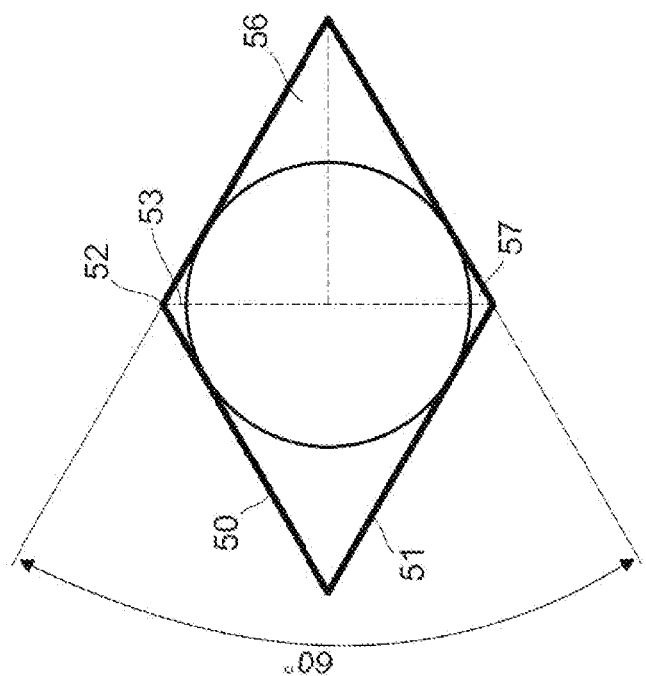
FIGS. 1G to 1J illustrate further examples of quadrangular basic shapes of receptacles of a holding structure provided according to the present invention.
Figure 1G:
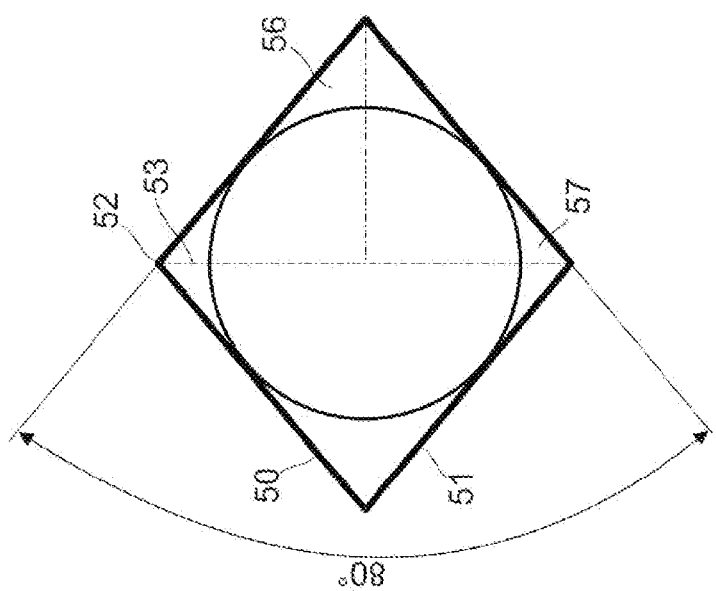
Figure 1J:
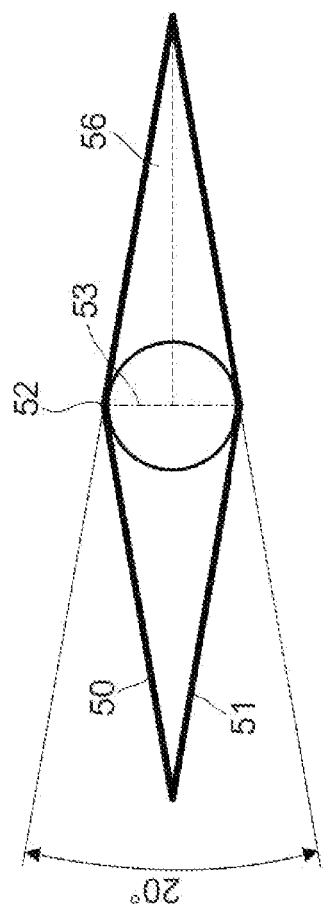
Figure 1I:
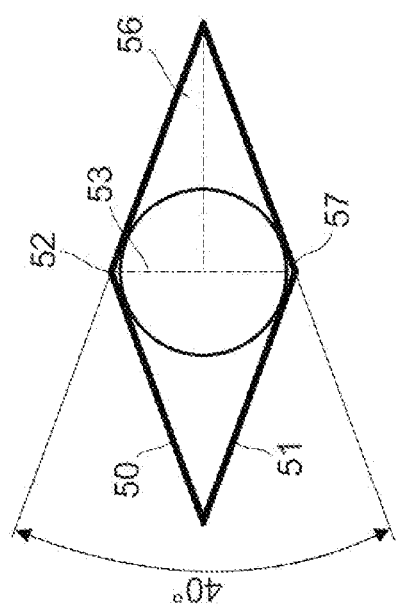

Some exemplary geometries for holding structures (so-called nests) are described in more detail below. Starting from the shape of a regular quadrangle, the receptacle according to FIG. 1G is compressed in a direction parallel to the axis of symmetry 53 and correspondingly expanded in a direction perpendicular thereto, which results in a convergence angle of the side walls 51, 52 in the region of the widened clearance 56 of 80°. In the example of FIG. 1H, the aforementioned compression and expansion is more strongly pronounced, which results in a convergence angle of the side walls 51, 52 in the region of the widened clearance 56 of 60°. In the examples of FIGS. 1I and 1J, the aforementioned compression and expansion is still more strongly pronounced, which results in a convergence angle of the side walls 51, 52 in the region of the expanded clearance 56 of 40° and 20°, respectively.

FIGS. 2A to 2E illustrate details of a holding structure 1 having, as viewed in plan view, diamond-shaped receptacles 5 which are arranged in a regular arrangement on a carrier 2. To facilitate handling of the holding structure 1, its upper side is formed as a plate-shaped carrier 2 which expediently has rounded-off corners 4. Access openings 9 in the upper side 2 serve for gripping the holding structure 1, said openings being provided offset to one another on two mutually opposite sides of the holding structure 1. Also formed at a number of positions in the plate-shaped carrier 2 are openings 25 as through-holes which can serve in particular as positioning holes in order to allow the possibility that the holding structure 1 can be oriented in a positionally accurate manner on a holding structure receptacle having corresponding positioning pegs or projections, which is, for example, particularly useful during the insertion (nesting), filling, closing or removal (denesting) of the containers received in the holding structure.

Figure 2A:
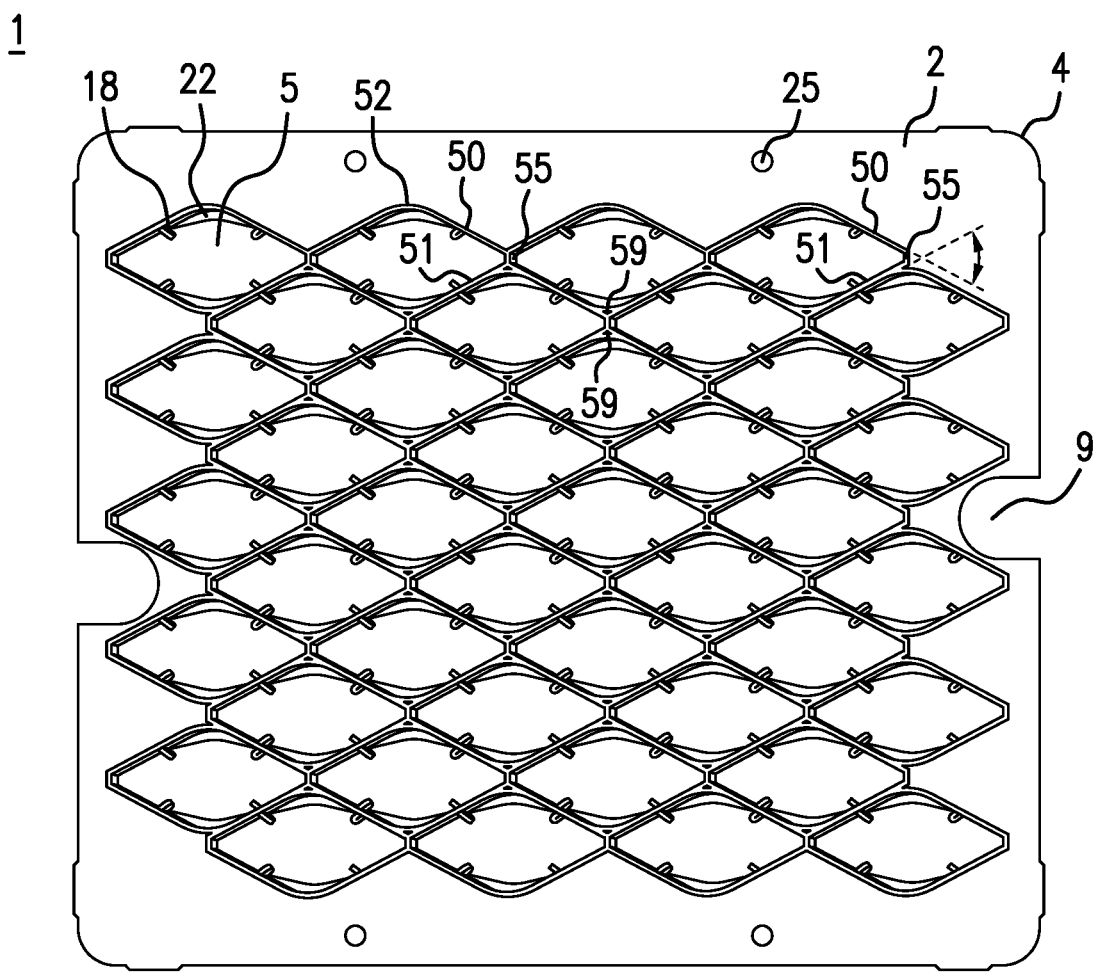
FIG. 2A illustrates a holding structure provided according to an exemplary embodiment of the present invention having a plurality of receptacles that have the basic shape according to FIG. 1D in a plan view.
Figure 2B:
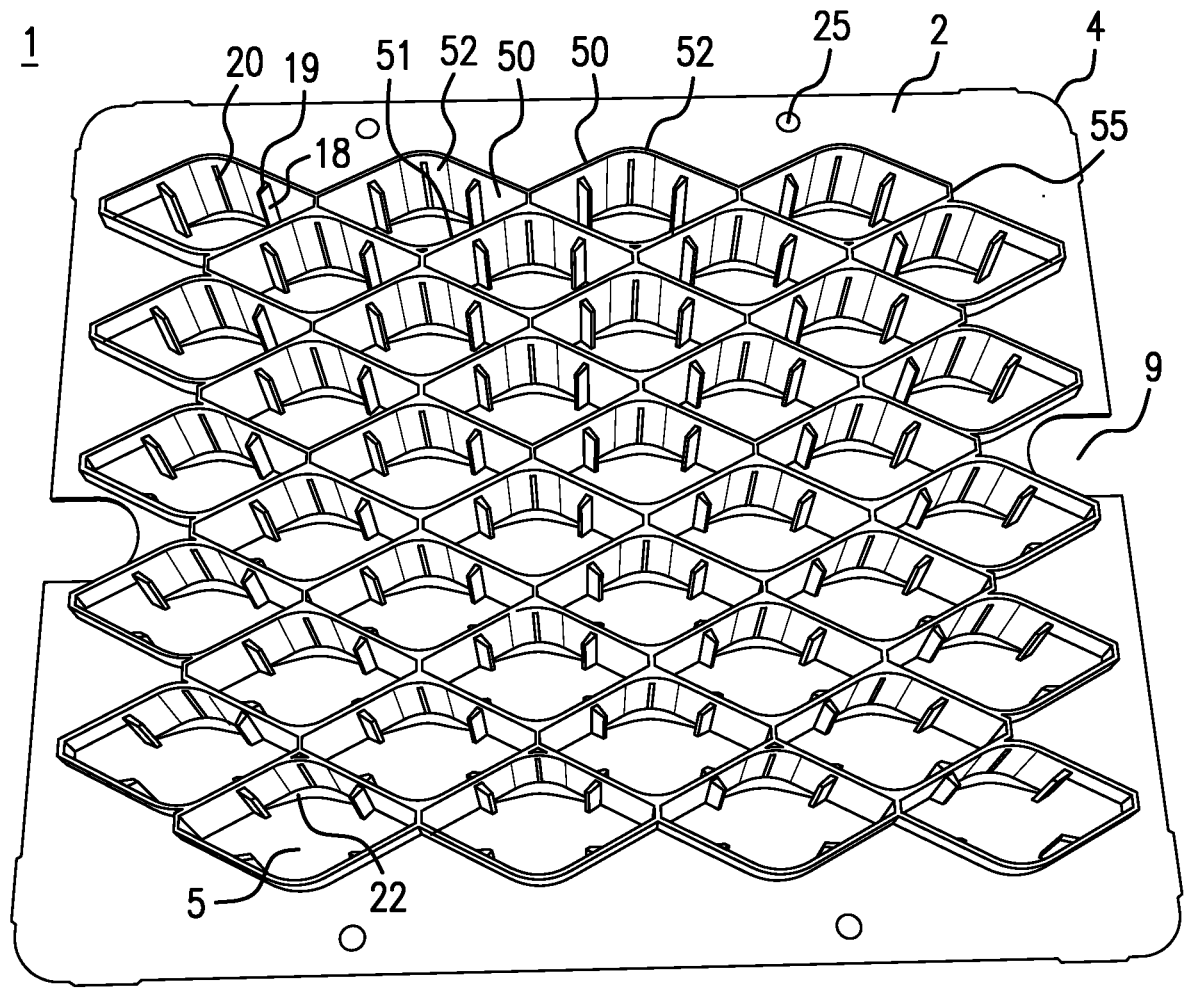
FIG. 2B illustrates the holding structure according to FIG. 2A in a perspective plan view.
Figure 2C:
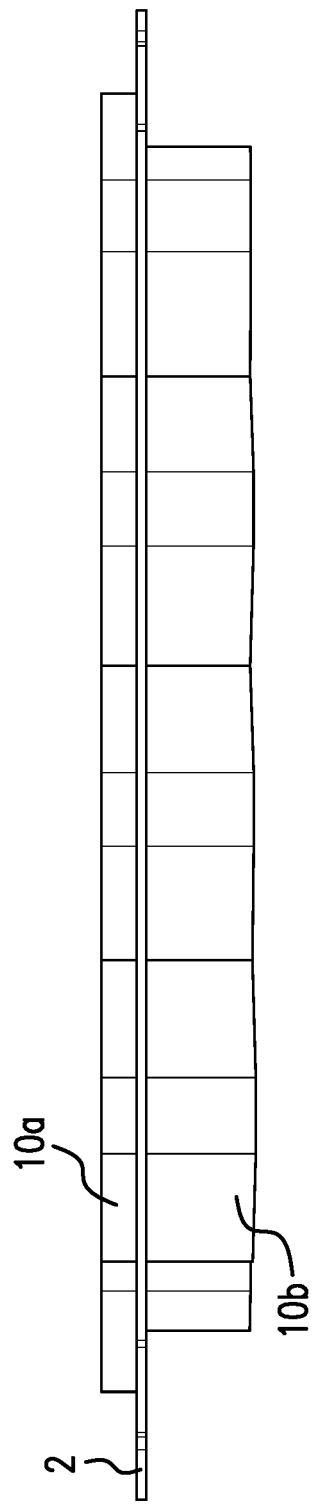
FIG. 2C illustrates the holding structure according to FIG. 2A in a side view.

As can be gathered from FIG. 2C, the side walls 10a, 10b project at a right angle both from the upper side of the carrier 2 and from the lower side of the carrier 2.

As illustrated in FIGS. 2A and 2B, the side walls 50, 51 converge at an angle ?, not, however, in a punctiform corner region but in a comparatively short connecting web 55. The apexes 52 of the side walls 50, 51 can have a profile which is concavely curved in an arc shape.

As illustrated in FIG. 2A, in the hexagonal arrangement of the receptacles 5 that is illustrated, in each case four side walls 50, 51 converge in the comparatively short connecting webs 55. The side walls 50, 51 and connecting webs 55 of directly adjacent receptacles 5 are formed in one piece with one another, without the formation of double-walled structures, as is frequently the case in conventional holding structures. Nor are any double-walled structures present on the lower side of the holding structure 1, with the result that the holding structure 1 has an advantageously high intrinsic stiffness even with a small wall thickness of the side walls 51 and connecting webs 55 and of the upper side 2.

Figure 2D:
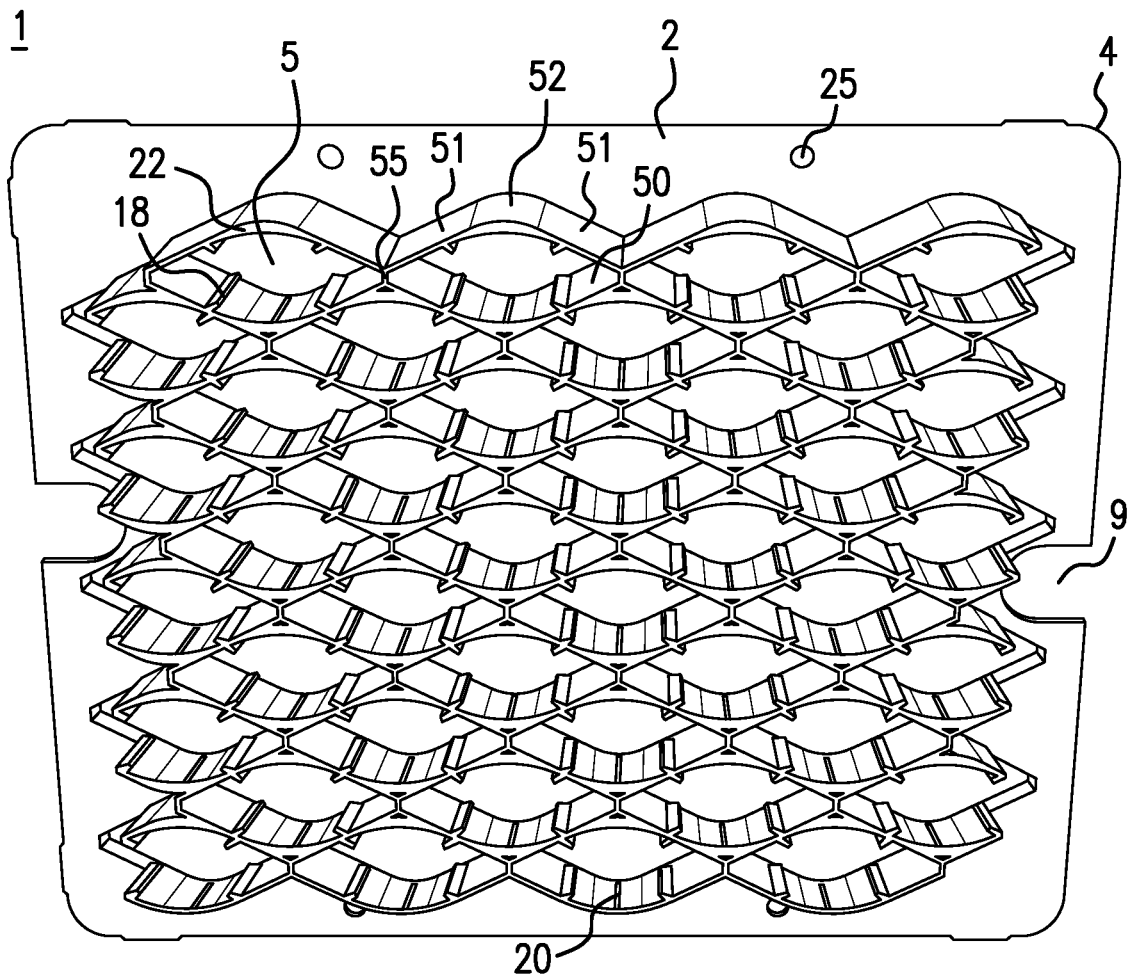
FIG. 2D illustrates the holding structure according to FIG. 2A in a perspective view from below.
Figure 2E:
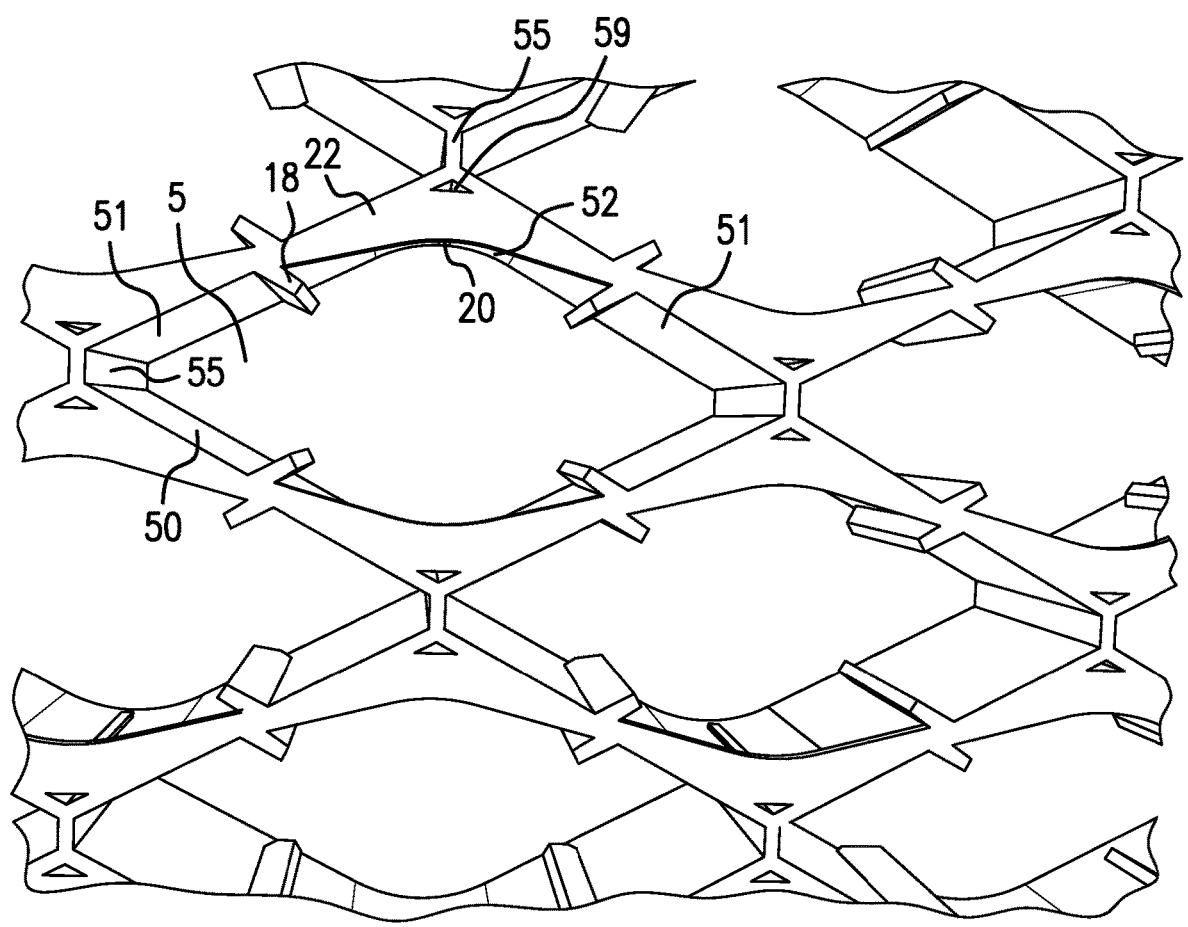
FIG. 2E illustrates the holding structure according to FIG. 2A in a greatly enlarged partial view from below.

According to FIG. 2D, holding projections 22 which act as holding portions are provided on the lower ends of the receptacles 5 and extend radially inwardly into the receptacles Each receptacle 5 expediently has two holding projections 22 which are situated diametrically opposite one another. The holding projections 22 limit the axial movability of the containers received in the receptacles 5 by a form fit and hold the containers in the receptacles 5, as described in more detail below. In principle, an individual holding projection 22 is also sufficient for this purpose, which projection can also be designed to be peripheral or substantially peripheral.

The side walls 50, 51 and connecting webs 55 of directly adjacent receptacles 5 are in each case connected to one another or formed in one piece over the entire axial length of the receptacles 5. The point-symmetrical or substantially star-shaped connecting regions at the regions of the connecting webs 55 and apexes 52 ensure a uniform force flow. Overall, these measures increase the intrinsic stiffness of the holding structure 1.

Guide ribs 18 are provided on all the side walls 50, 51 of the receptacles 5 and project radially inwardly into the receptacles 5, with the result that the side walls of the containers rest directly against the guide ribs 18 and are guided by the latter when inserted into the receptacles 5. The guide ribs 18 extend substantially over the entire length of the receptacles 5 in their longitudinal direction. The guide ribs 18 can start at a small distance from the upper side 2 of the holding structure 1 and in each case extend down to the lower end of the receptacles 5, to be more precise as far as the transition region to the holding projections 22. On the upper ends of the guide ribs 18 there can be formed insertion bevels 19 which are inclined at an acute angle relative to the guide ribs 18 (cf. FIG. 2B).

Figure 3A:
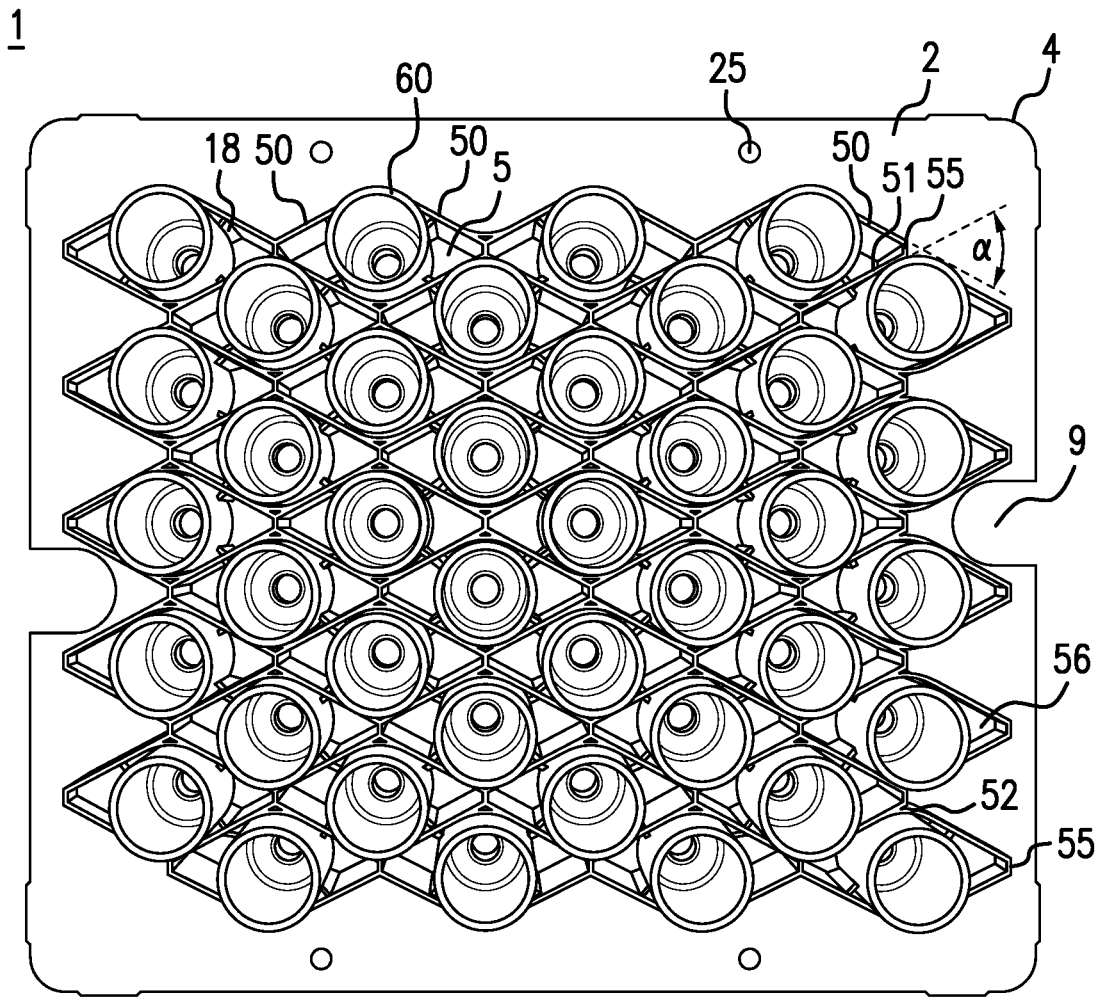
FIG. 3A illustrates in a schematic plan view a combination of a holding structure according to FIG. 2A and a plurality of carpoules which are held on the holding structure as intended.
Figure 3B:
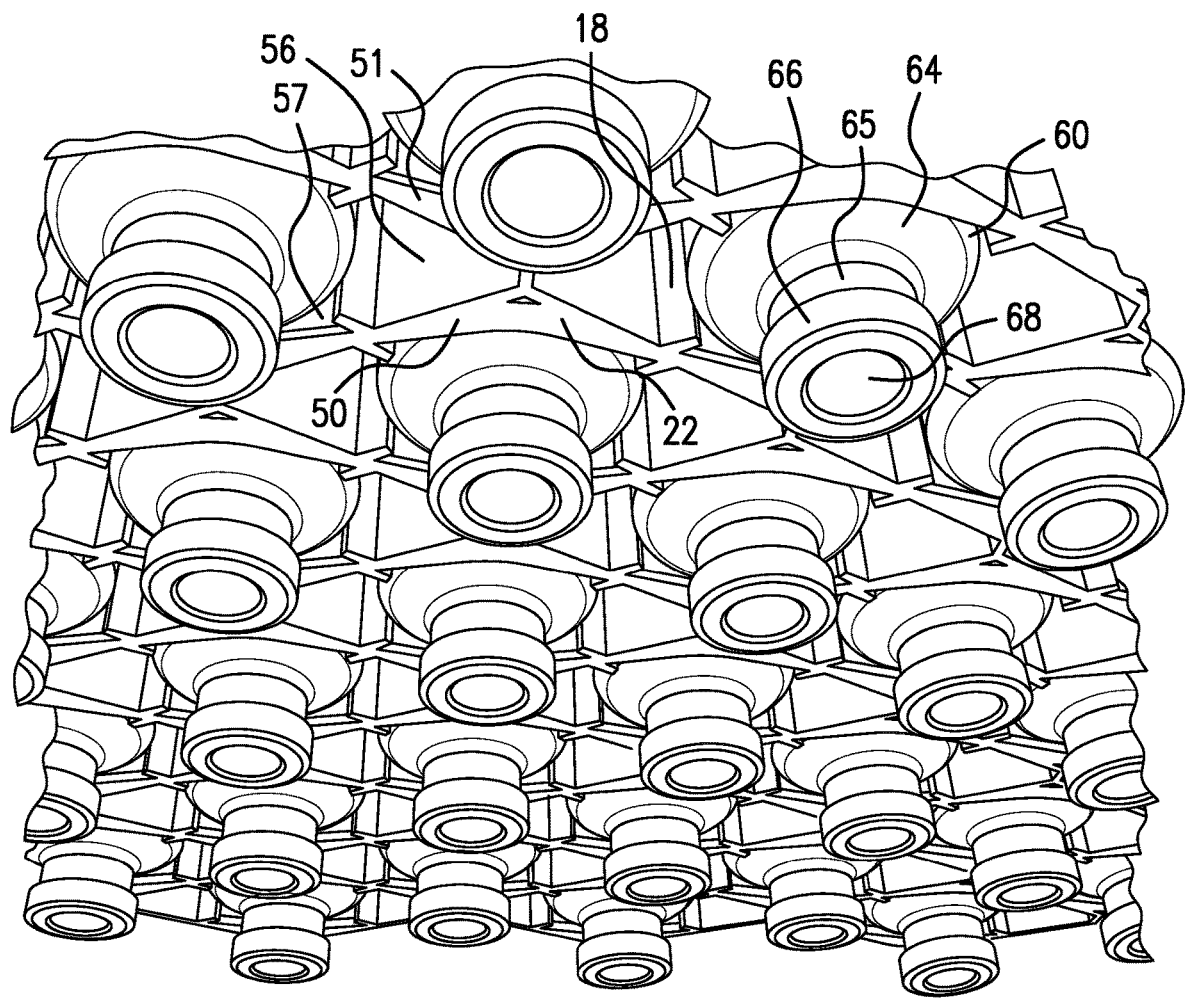
FIG. 3B illustrates the combination according to FIG. 3A in an enlarged perspective partial view from below.
Figure 3C:
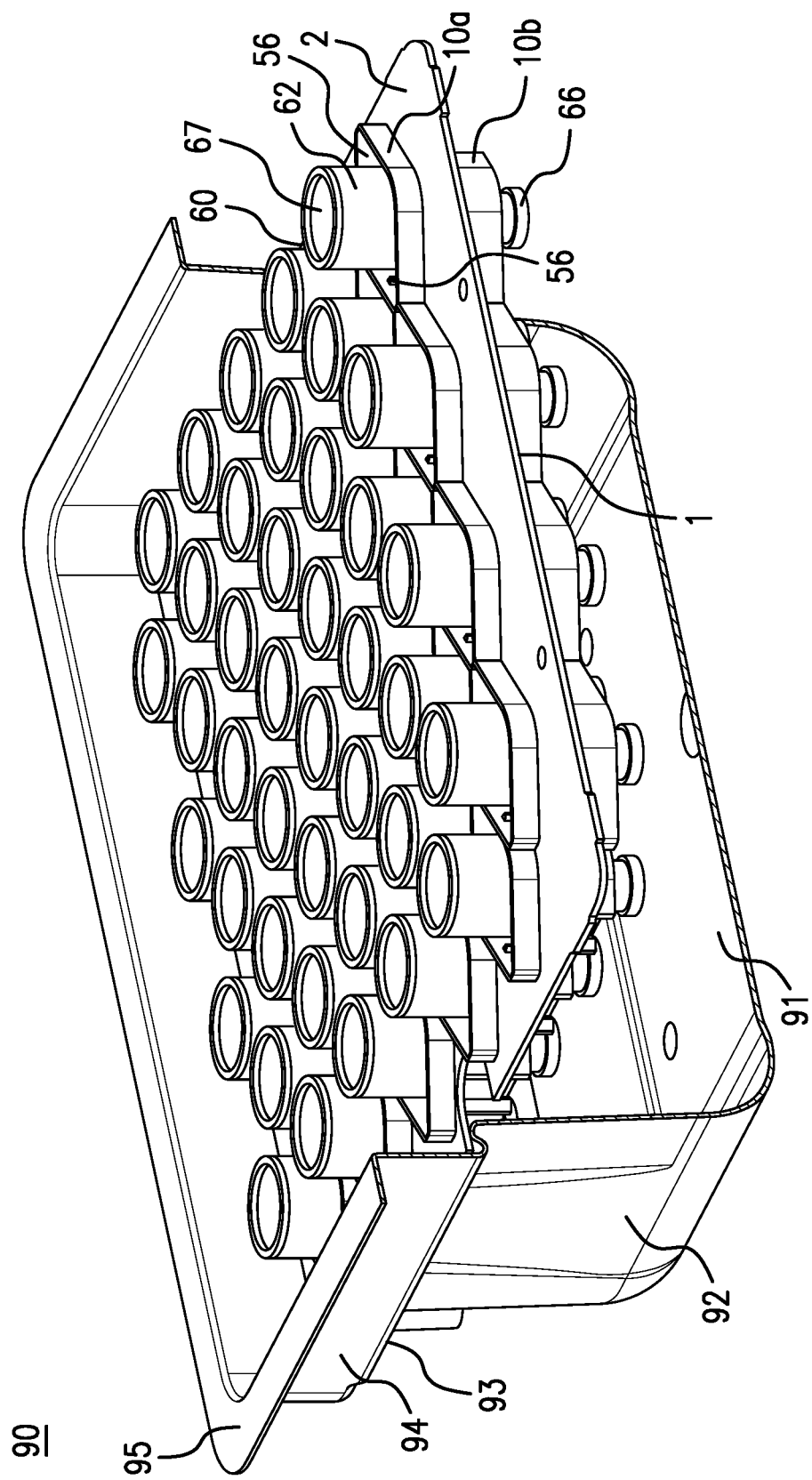
FIG. 3C illustrates in a schematic partial section the reception of the combination according to FIG. 3A in a transport and packaging container.

FIGS. 3A to 3C illustrate by way of example how carpoules 60 are held on a holding structure 1 provided according to the present invention. Carpoules 60, like other pharmaceutical containers, customarily have a main body which is formed by a cylindrical side wall 62 which is adjoined by a tapered shoulder portion 64 and a narrowed neck portion 65 which merges into a widened upper edge 66 having an ejection opening 68 formed therein which is customarily closed by a plug with a septum or the like which is axially secured on the upper edge 66 with a crimped-on metal cover. At an opposite end there is situated a filling opening 67 for filling and subsequently receiving a plunger. The carpoules 60 are received upside down in the receptacles 5 of the holding structure 1, wherein the shoulder portion 64 is supported directly on the two holding projections 22, and the end with the widened upper edge 66 (and where present with the plug fitted thereon and metal cover) extends through the interspace between the two mutually opposite holding projections 22 and is freely accessible from the lower side of the receptacles 5. In this state, the ends with the filling openings 67 project a little beyond the upper edge of the upper side walls 10a on the upper side of the carrier 2 out of the receptacles 5. In the receptacles 5, the carpoules 60 are centered by the guide and positioning ribs 18 in the receptacles 5. According to FIG. 3B, a widened clearance 56 is formed on both sides of the carpoules 60 and allows access to the carpoules 60, which are received in the receptacles 5, for their handling (for example gripping, lifting or the like). Here, access can be had from the upper side and/or from the lower side of the carrier 2, as described below.

FIG. 3C further illustrates the arrangement of a combination of a holding structure 1 and a plurality of carpoules 60 held thereon in a transport and packaging container 90. According to FIG. 3C, the transport and packaging container 90 is substantially box- or trough-shaped and has a bottom 91, a peripherally formed side wall 92 projecting perpendicularly therefrom, a step 93 projecting substantially at a right angle from said side wall, a peripherally formed upper side wall 94 and an upper edge 95 which is formed in the manner of a flange. The holding structure 1 rests directly on the step 93 of the transport and packaging container 90, with the result that the holding structure 1 is positioned precisely in the transport and packaging container 90 and the plurality of carpoules 60 are in this way arranged and held in a regular arrangement and at precisely defined positions. A protective film (not illustrated) is applied to the upper edge 95 in a delivery state.

Figure 4A:
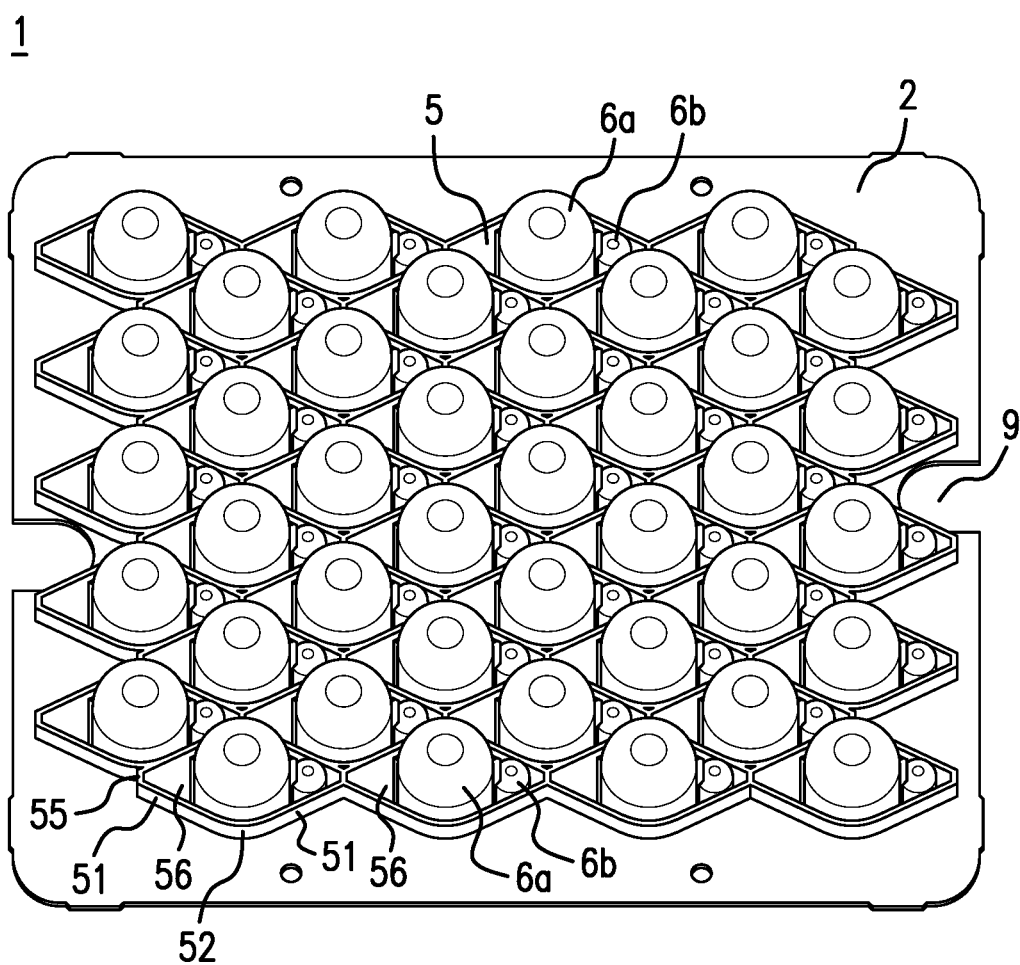
FIG. 4A illustrates in a perspective plan view a combination of a holding structure according to FIG. 2A and a plurality of complex medical assemblies which are held on the holding structure as intended.
Figure 4B:
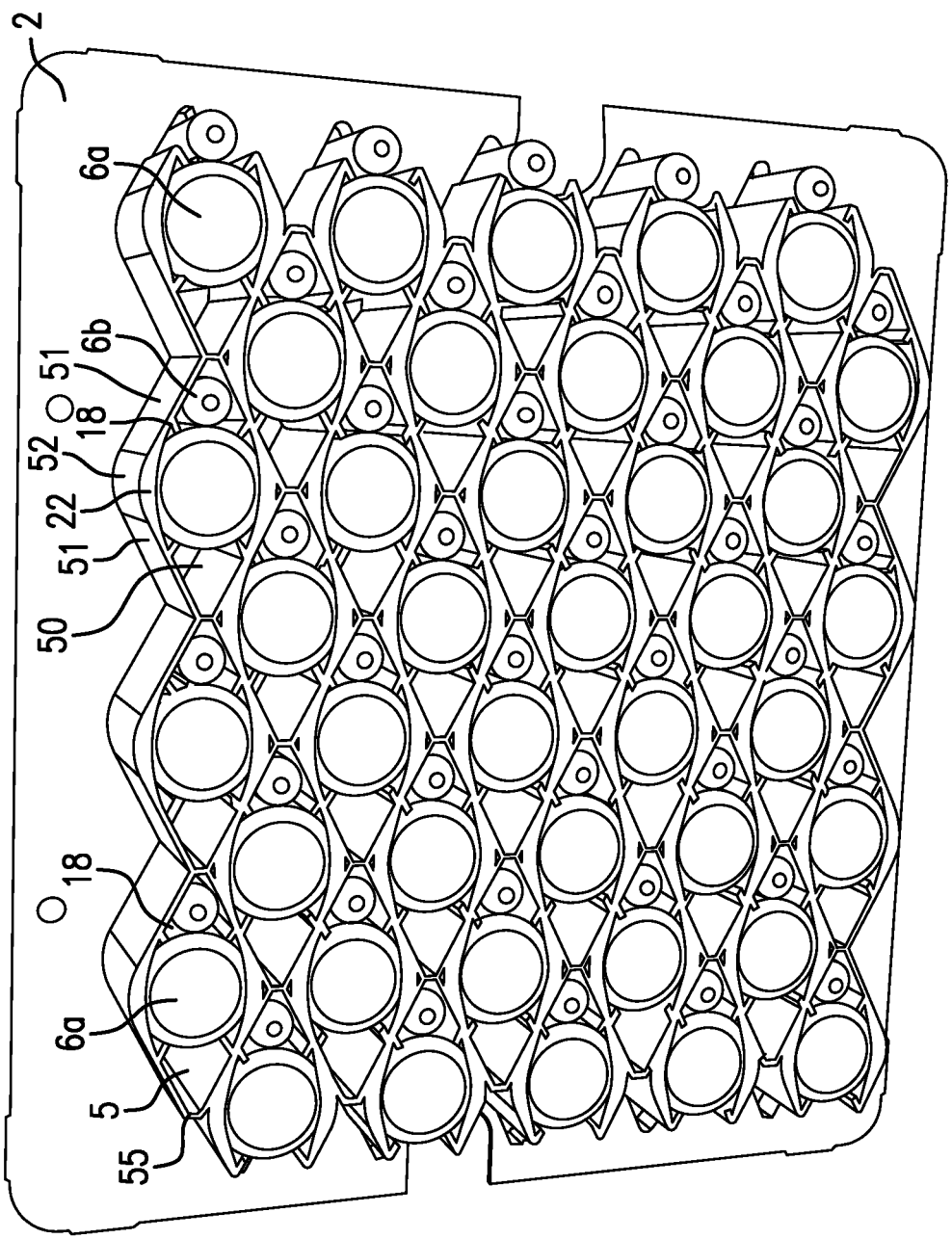
FIG. 4B illustrates the combination according to FIG. 3A in a perspective view from below.

FIGS. 4A and 4B illustrate by way of example how more complexly designed units are held on a holding structure 1 provided according to the present invention. It may be assumed in this example that the units have a main body 6a of a generally cylindrical basic shape and a lateral extension 6b which projects laterally from the main body 6a but is connected thereto. The main body 6a can contain, for example, a pharmaceutical container, for example a carpoule or a syringe body. Such units can, for example, constitute simple medical devices and can be used, for example, in injection pens or as auto-injectors for self-medication in diabetes or the like. As illustrated in FIGS. 4A and 4B, the lateral extension 6b almost completely fills one of the two widened clearances 56. For access to the unit for handling thereof, the opposite widened clearance 56 is nevertheless available. Here, access can be had from the upper side and/or from the lower side of the carrier 2, as described below.

Figure 5A:
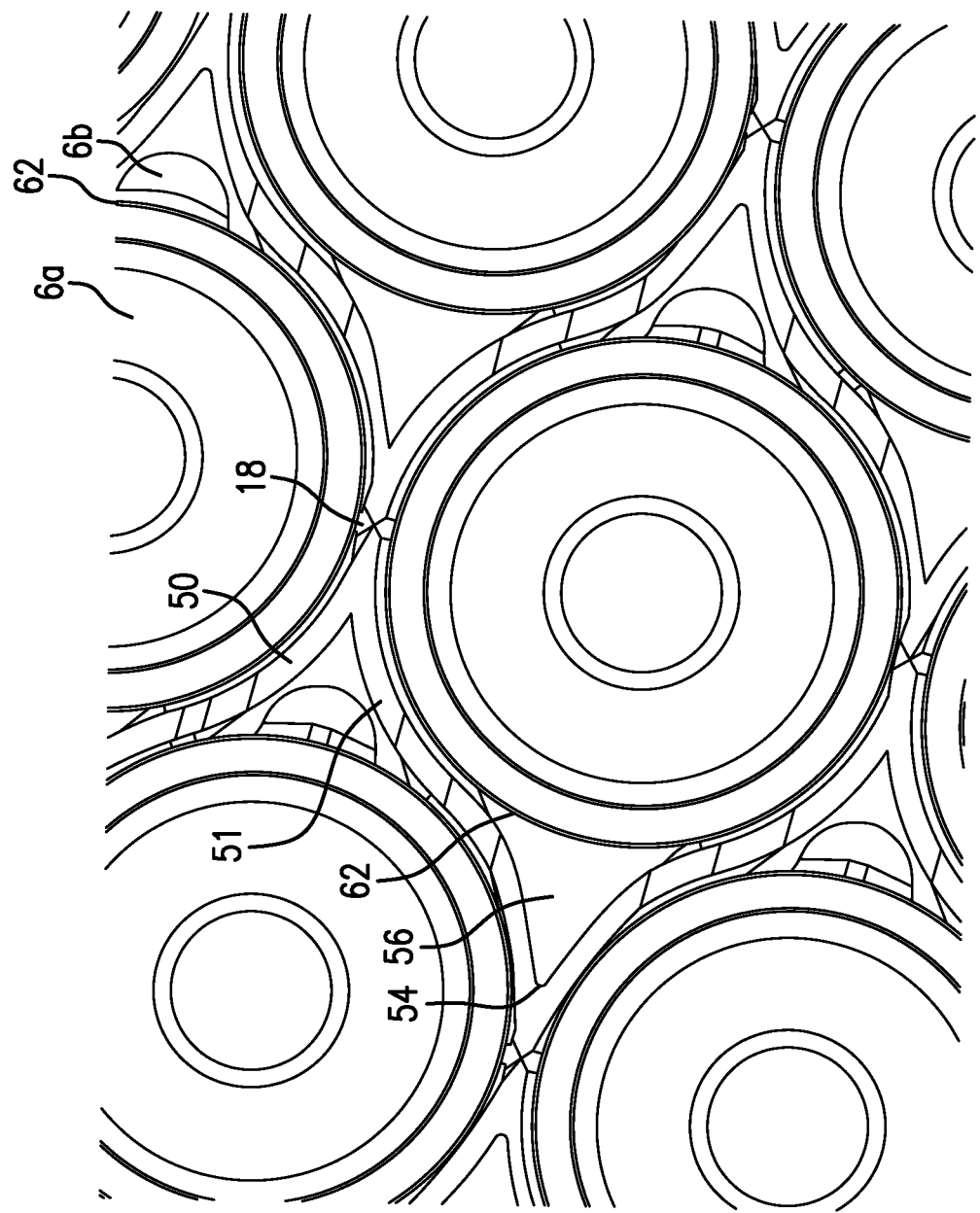
FIGS. 5A and 5B illustrate in a schematic partial plan view and in a perspective plan view the retention of bypass carpoules in receptacles of a holding structure provided according to an exemplary embodiment of the present invention.
Figure 5B:
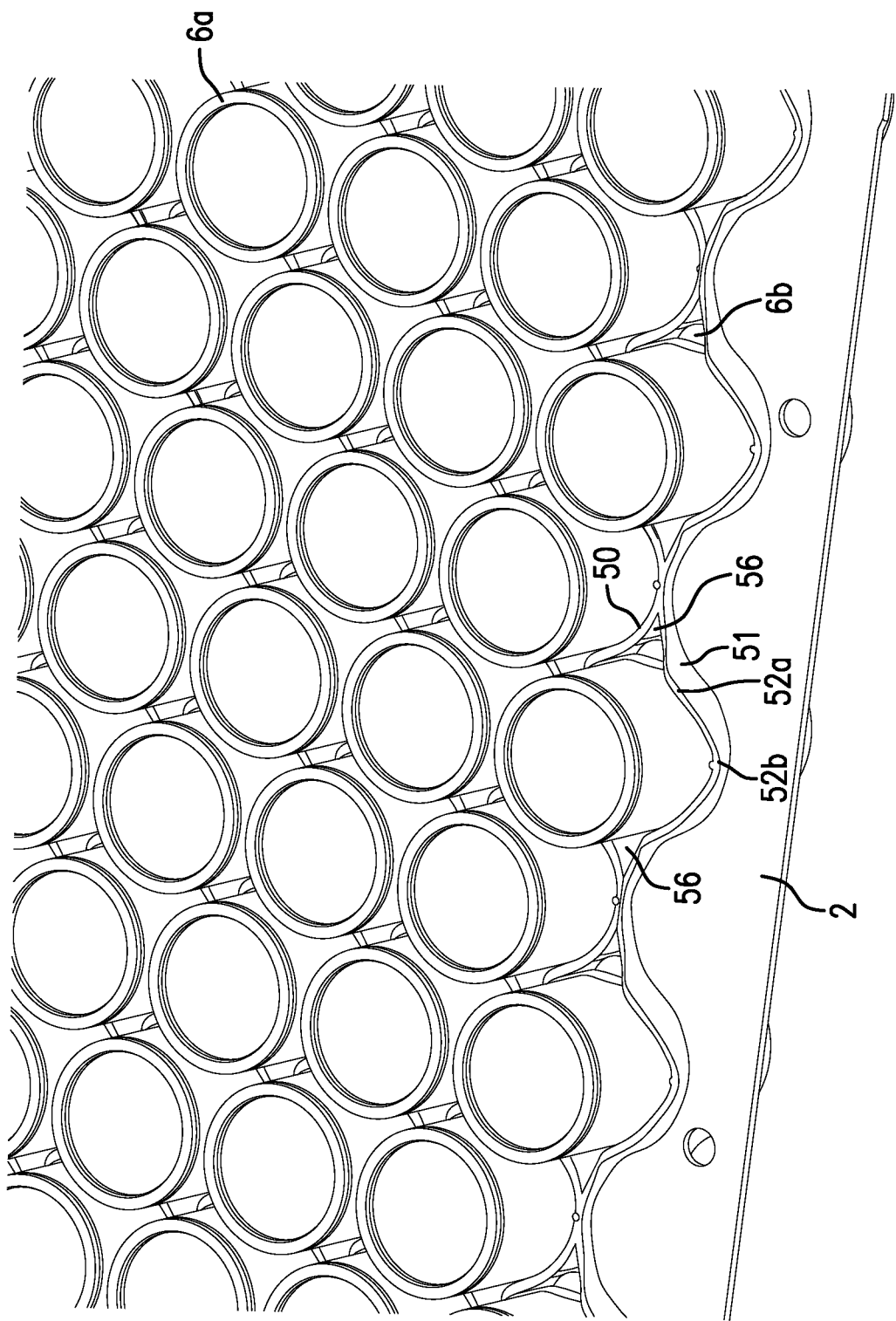
Figure 5C:
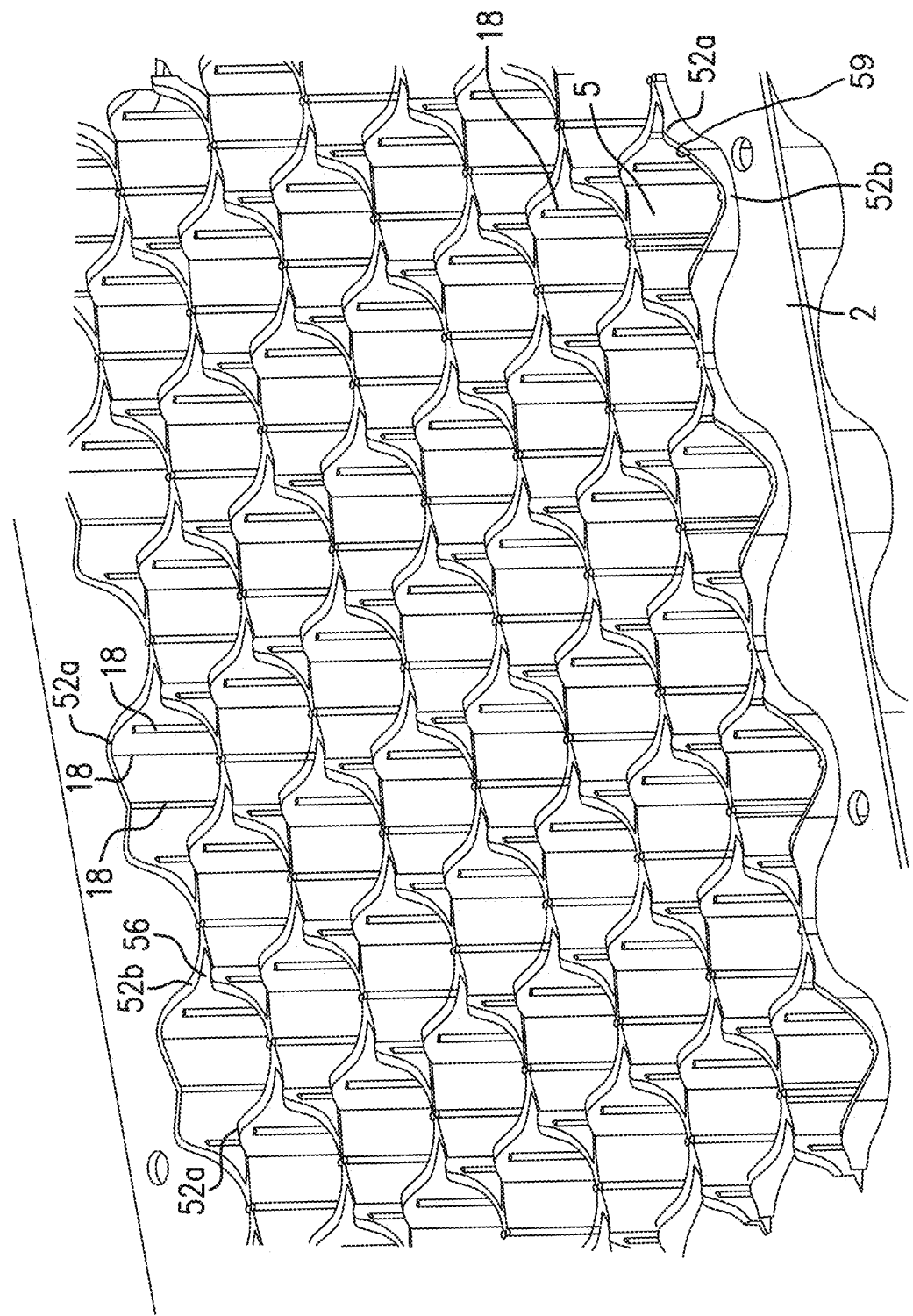
FIG. 5C illustrates the receptacles of the holding structure provided according to the exemplary embodiment of FIGS. 5A and 5B without bypass carpoules.

FIGS. 5A and 5B illustrate, in a schematic partial plan view and in a perspective plan view, the retention of bypass carpoules in receptacles of a holding structure according to a further exemplary embodiment provided according to the present invention. The carpoules have a cylindrical main body 6a and a lateral extension 6b which fills one of the two widened clearances 56 of the receptacles. For access to the bypass carpoule for handling thereof, the opposite widened clearance 56 is nevertheless available. Here, access can be had from the upper side and/or from the lower side of the carrier 2, as described below. FIG. 5C illustrates the receptacles of this holding structure without bypass carpoules.

According to FIGS. 5A to 5C, the two side walls 50, 51 are curved in an arc shape and they converge in the two corner regions 54 of a receptacle tangentially or so as to enclose a comparatively small acute angle, for which the following holds: $\alpha<55°$, such as $\alpha<45°$ or $\alpha<30°$. The apexes of the side walls 50, 51 are concavely curved, and guide and positioning ribs 18 are provided in the region thereof. As can be gathered from FIGS. 5B and 5C, the upper edge of the peripheral side walls of the receptacles forms a closed, smooth curve having at least one local maximum 52a and at least one local minimum 52b in a direction perpendicular to the upper side of the holding structure. To be more precise, the upper edges of the side walls have in each case four local maxima 52a and local minima 52b. Two local minima 52b are situated in the region of a respectively assigned widened clearance 56. The upper edge of the receptacles thus forms a type of slide or inclined ramp 59 which allows an angular orientation of the bypass carpoules with their asymmetrical basic shape. The bypass carpoules, which are wider in a first direction than in a direction perpendicular thereto, are, during insertion into the receptacles 5, automatically guided vertically from above and rotated in such a way that the first direction in which the bypass carpoules are wider is automatically oriented parallel to the direction of the receptacles 5 in which the receptacles 5 are wider. This allows an automatic angle of rotation orientation of the bypass carpoules.

Figure 6A:
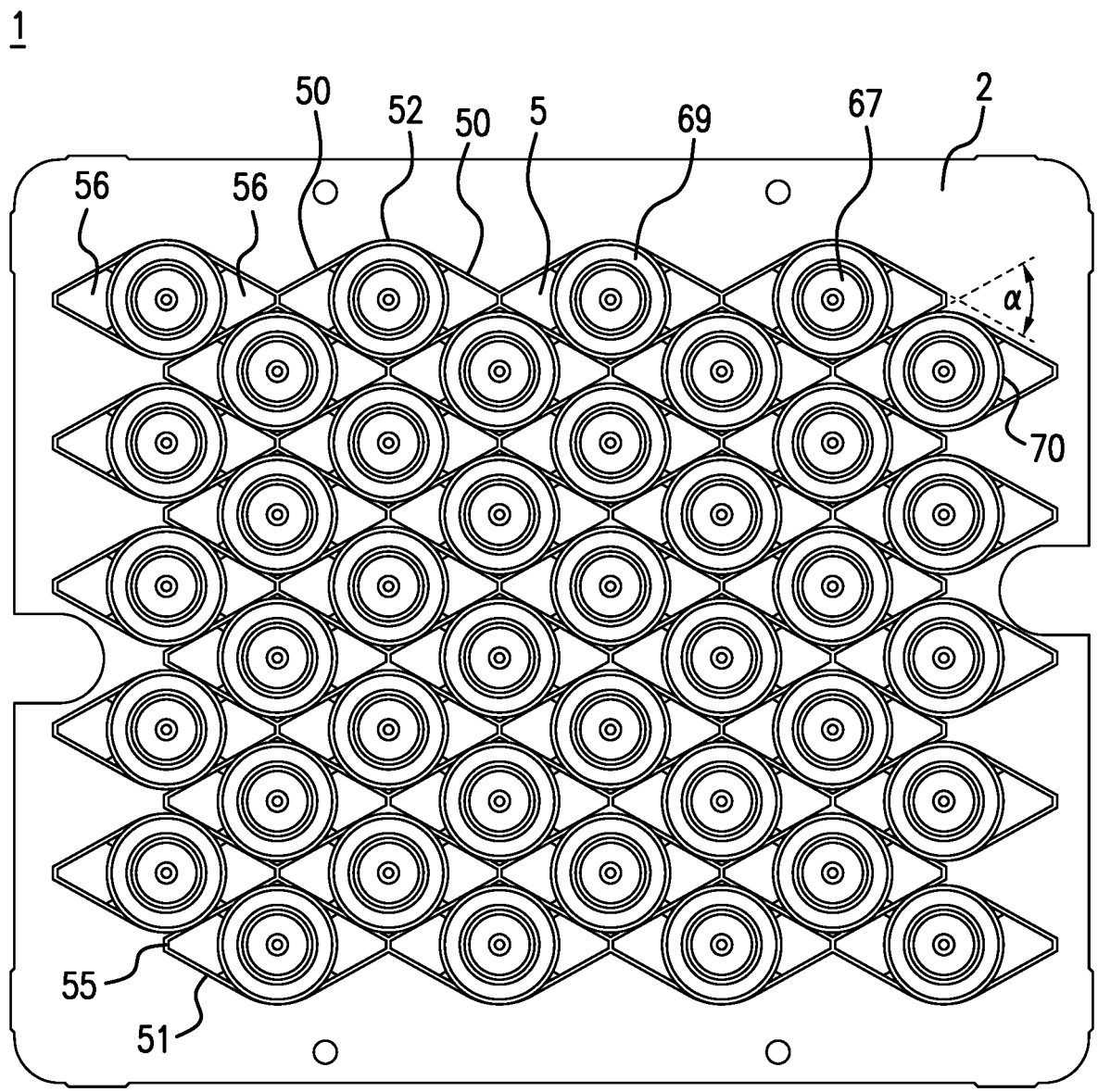
FIG. 6A illustrates in a perspective plan view a combination of a holding structure according to FIG. 2A and a plurality of syringe bodies which are held on the holding structure as intended.
Figure 6B:
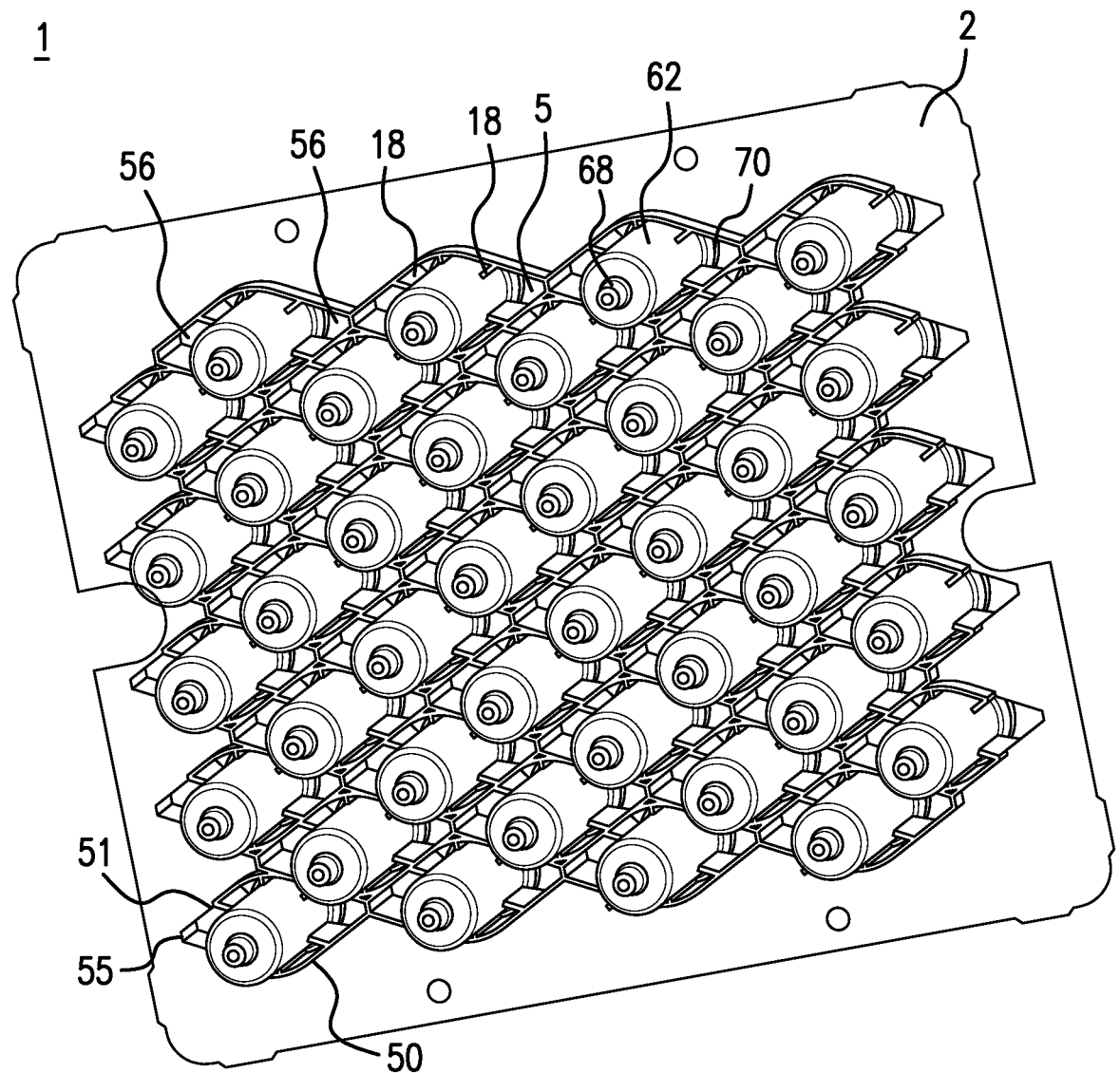
FIG. 6B illustrates the combination according to FIG. 6A in a perspective view from below.

FIGS. 6A and 6B illustrate by way of example how syringe bodies 69 are held on a holding structure 1 provided according to the present invention. The syringe bodies 69 customarily have a main body on whose distal end there is formed an ejection opening 68. On an opposite end there is situated a filling opening 67 for filling and subsequently receiving a plunger. The syringe bodies 69 are received upside down in the receptacles 5 of the holding structure 1, wherein the widened flange 70 lies on the upper ends of the side walls 50, 51 on the upper side of the carrier 2. In this state, the syringe bodies 69 are centred by the guide and positioning ribs 18 in the receptacles 5. According to FIG. 6B, a widened clearance 56 is formed on both sides of the carpoules 60 and allows access to the syringe bodies 69, which are received in the receptacles 5, for their handling (for example gripping, lifting or the like). Here, access can be had from the upper side and/or from the lower side of the carrier 2, as described below.

Figure 7A:
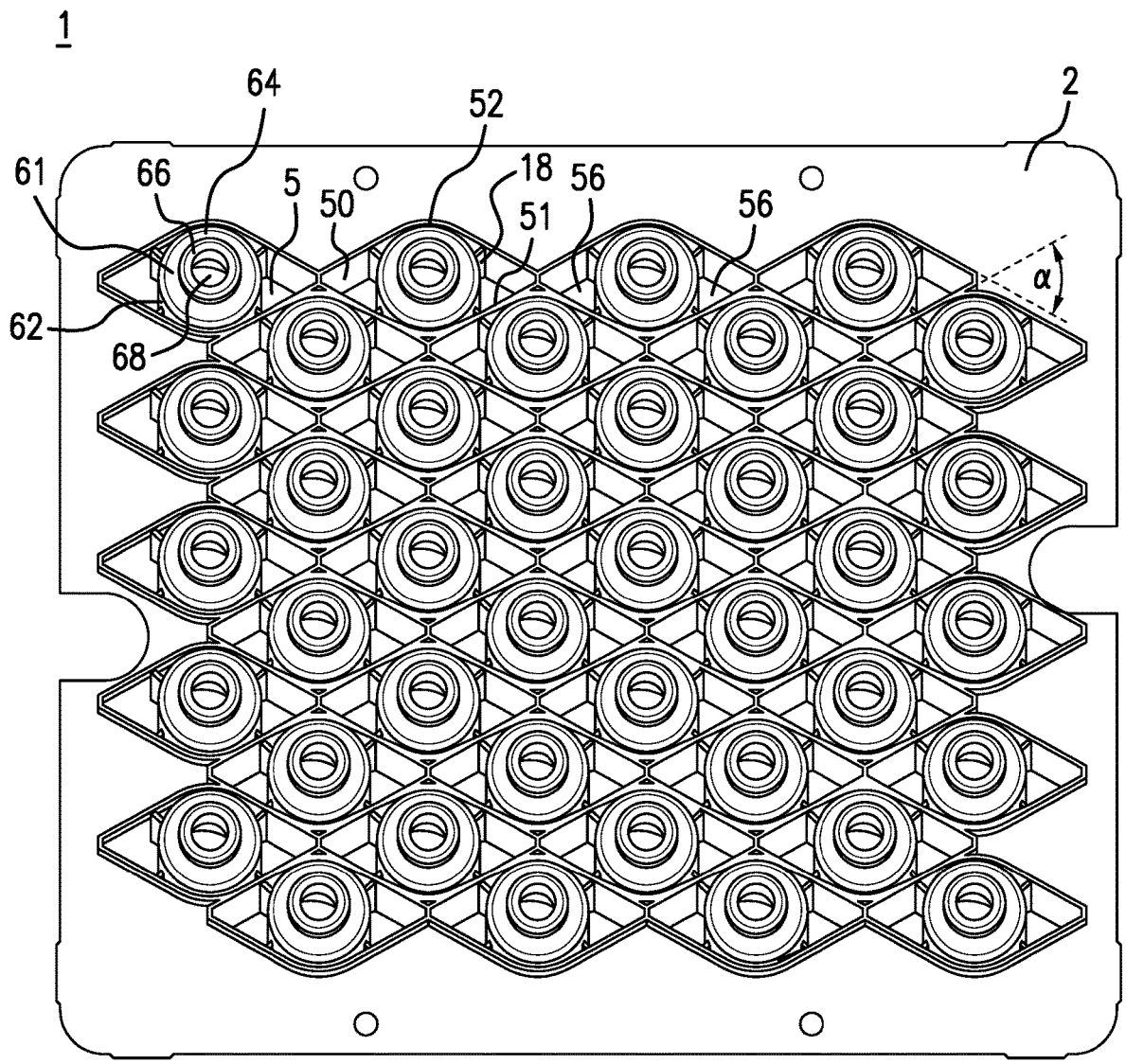
FIG. 7A illustrates in a perspective plan view a combination of a holding structure according to FIG. 2A and a plurality of vials which are held on the holding structure as intended.
Figure 7B:
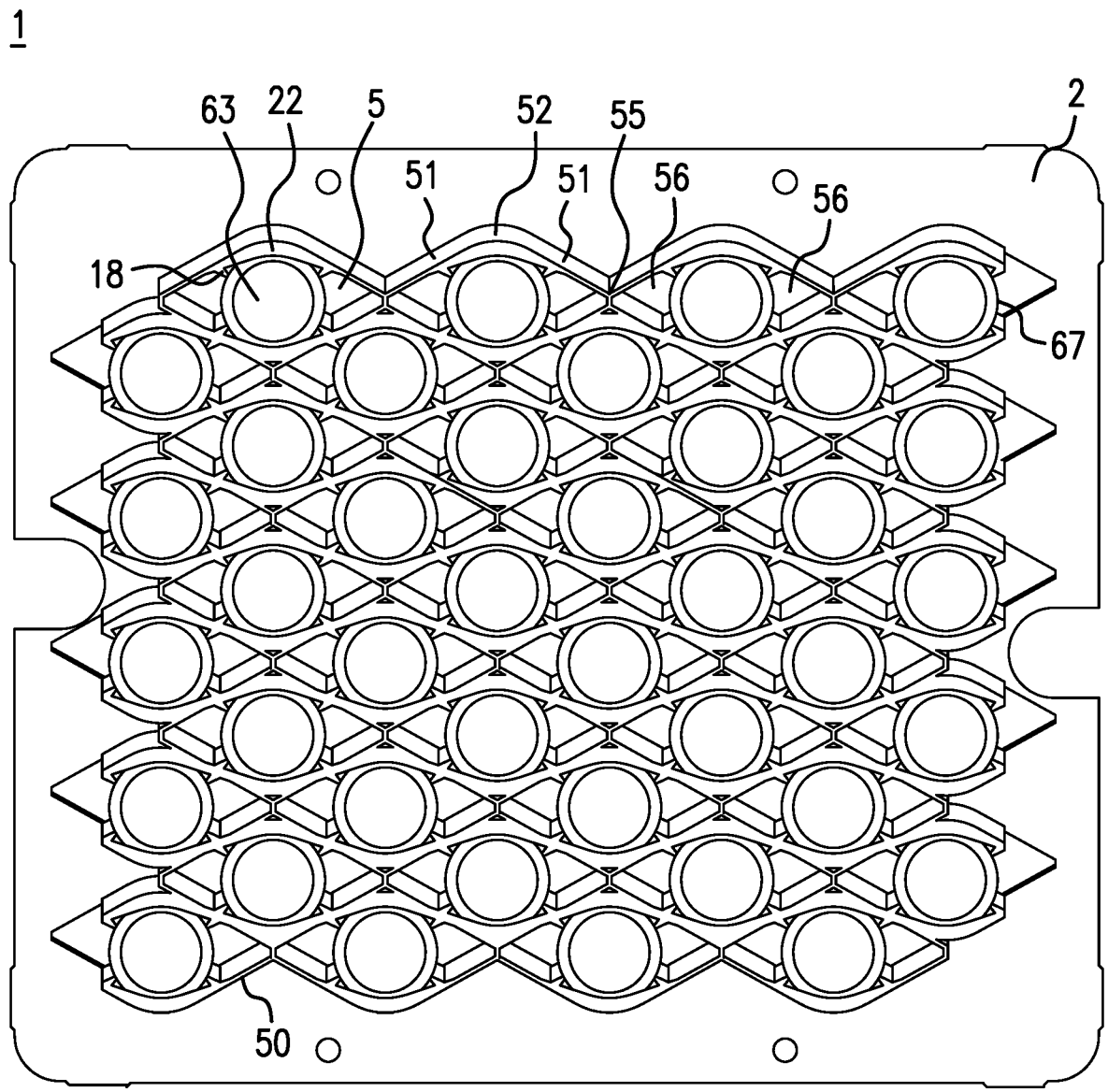
FIG. 7B illustrates the combination according to FIG. 7A in a bottom view.

FIGS. 7A and 7B illustrate by way of example how glass vials 61 are held on a holding structure 1 provided according to the present invention. The vials 61 customarily have a main body which is formed by a cylindrical side wall 62 which is adjoined by a tapered shoulder portion 64 and a narrowed neck portion which merges into a widened upper edge 66 with an ejection opening 68 formed therein which is customarily closed by a plug or the like which is axially secured to the upper edge 66 with a crimped-on metal cover. At an opposite end, the vial 61 is formed with a closed bottom 63. According to FIG. 7B, the vials 61 are received upright in the receptacles 5 of the holding structure 1, wherein the bottom 63 is directly supported on the two holding projections 22 and is accessible from the lower side of the receptacles 5. In this state, the ends with the filling openings 67 project a little beyond the upper edge of the upper side walls 50, 51 on the upper side of the carrier 2 out of the receptacles 5. In the receptacles 5, the carpoules 60 are centred by the guide and positioning ribs 18 in the receptacles 5. According to FIG. 7A, a widened clearance 56 is formed on both sides of the vials 61 and allows access to the vials 61, which are received in the receptacles 5, for their handling (for example gripping, lifting or the like). Here, access can be had from the upper side and/or from the lower side of the carrier 2, as described below.

Figure 8A:
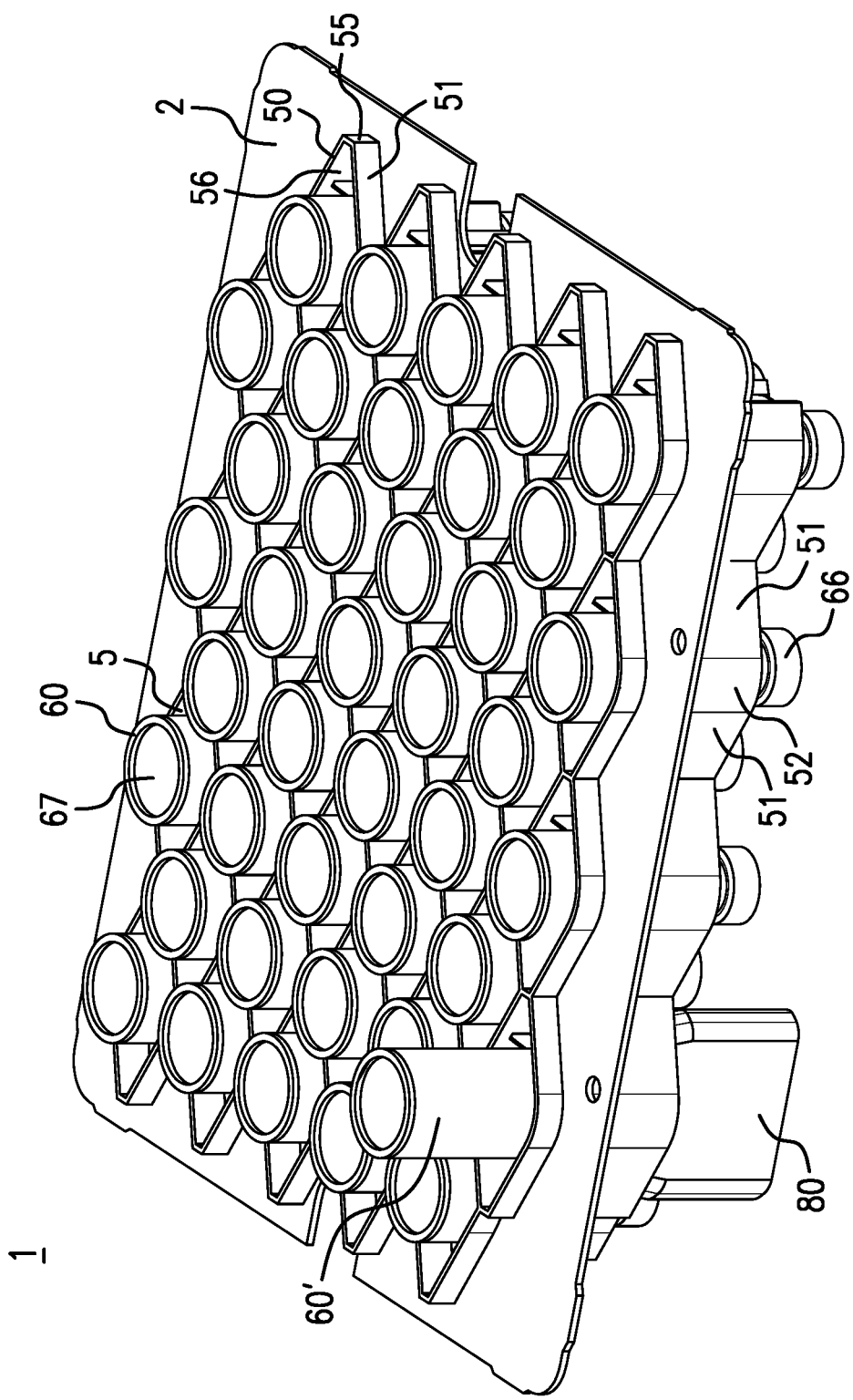
FIG. 8A illustrates in a perspective plan view the lifting of a carpoule in a combination according to FIG. 3A by a tool which, according to the present invention, engages in the clearances of a receptacle assigned to the carpoule.
Figure 8B:
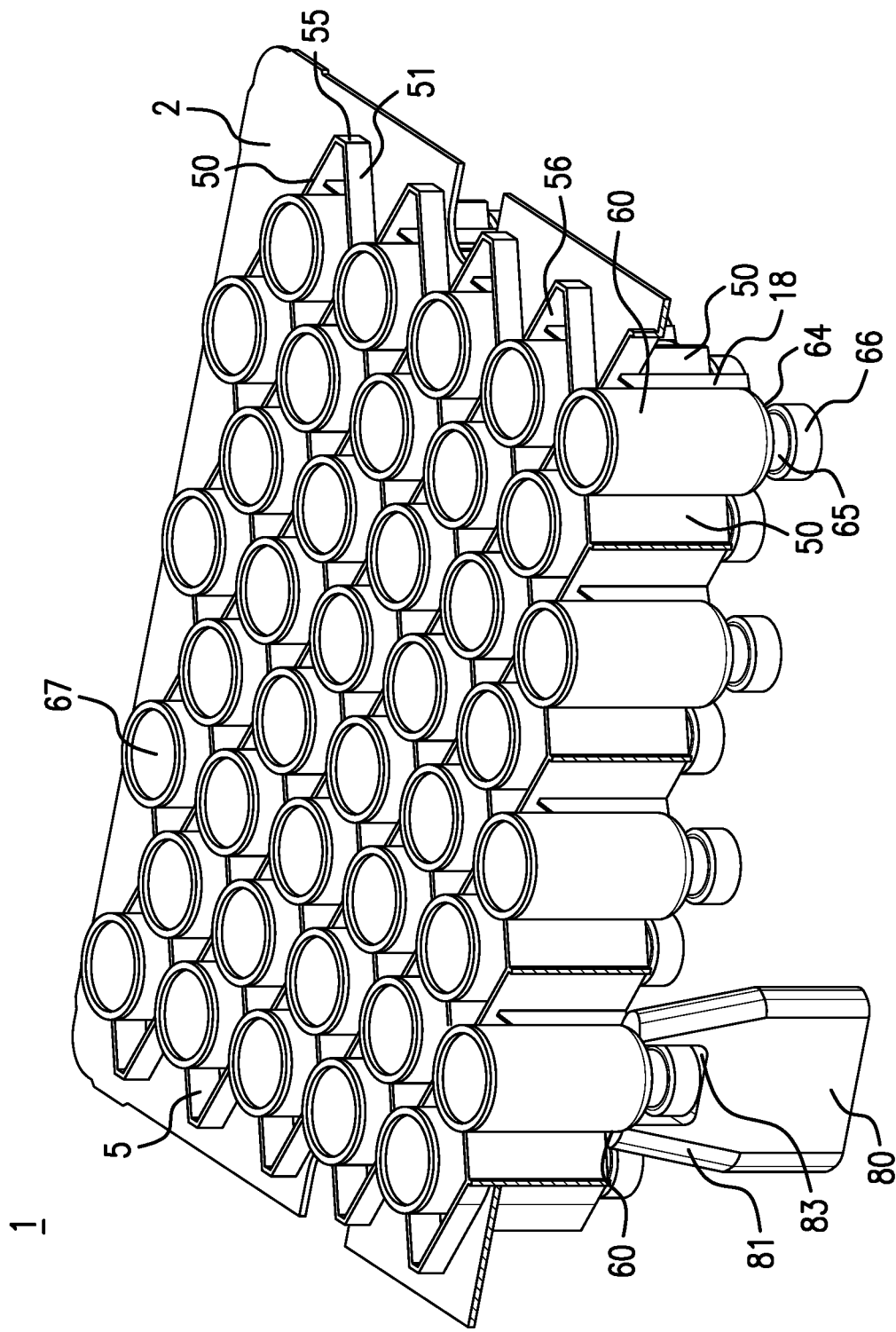
FIG. 8B illustrates the supporting of a carpoule in a combination according to FIG. 8A in a perspective partial section prior to lifting the carpoule.

With reference to FIGS. 8A to 8C, there is given below, as an example of the handling of pharmaceutical containers according to the present invention, the lifting of a carpoule 60 in a combination by a tool which according to the present invention engages in the widened clearances 56 of a receptacle 5, which is assigned to the carpoule 60, of the holding structure 1. According to FIGS. 8B and 8C, the tool 80 for handling has a rectangular basic body on whose upper end there are provided two handling arms 81 which converge towards one another at a small acute angle and, if appropriate, can be jointly pivoted about a common pivot point in the manner of tongs. Between the handling arms 81 there is formed a recess 83 into which there can project the widened upper edge 66 of the carpoule 60 with the metal cover possibly fastened thereon. The distance between the two handling arms 81 is chosen at their free upper ends 82 in such a way that said distance substantially corresponds to the outside diameter of the shoulder portion 64 of the carpoule 60. The width of the tool 80 is tailored to the dimensions of the receptacles 5 in such a way that the tool 80 can be inserted to a sufficient extent into the receptacles 5 in order to lift the carpoules 60.

Upon insertion of the tool 80 from the lower side of the carrier 2 into the receptacles 5, the free upper ends 82 of the handling arms 81 finally come into contact with the shoulder portion 64 of a carpoule 60, as illustrated in FIG. 8B. During further lifting of the tool 80, the carpoule 60 is thus lifted into a lifted position 60', as illustrated in FIGS. 8A and 8C. In this lifted state 60', the carpoule 60 can be gripped by a gripping tool and transported away or be held for further treatment while the carpoule 60 is still partially received in the receptacles 5.

It is also possible in the same manner, by a modified tool, for whole rows or columns of carpoules 60 or for all carpoules 60 held on a holding structure 1 to be simultaneously handled, for example be lifted or gripped. A tool designed in such a way can also be used for mechanically supporting the carpoules 60 if, for example, axially downwardly acting forces act on the carpoules 60, as is the case, for example, when placing plugs into the filling openings 67, in order thereby to counter bending of the carrier 2.

The handling arms 81 of the tool 80 can also be adjustable, for example to carry out a tongs like coordinated pivoting movement for gripping and releasing again a carpoule 60 received in a receptacle 5.

The intrinsic stiffness of the holding structure 1 particularly also allows further processing of the containers while they are received in the receptacles 5. It is conceivable, for example, that a holding structure 1 is placed along the edge of its lower side on a holding frame and then closure elements, for example closure plugs, are fitted onto the ends of the containers and the latter are displaced axially, such as at the same time for all the containers received in the holding structure or for one or more rows of containers. The forces predominant here are compensated for to a sufficient extent by the holding structure, with the result that only slight bending of the holding structure occurs (for example of at most 2.0 mm over the length of the holding structure), with the result that jamming of the closure elements can be avoided.

There is described below, with reference to FIGS. 9A to 9H, the insertion and holding of containers or medical devices which have a non-cylindrical basic shape. For such containers or medical devices, which are generally designated by the reference sign 6' and have already been taken above as the basis for FIGS. 4A and 4B, it is assumed below that they have a main body 6a, which has a cylindrical or substantially cylindrical basic shape, and a lateral extension 6b projecting laterally therefrom, from which it may be assumed here for reasons of simplification that said extension has a cylindrical or substantially cylindrical basic shape, but this is not absolutely necessary. The lower end of the main body 6a is designated by the reference sign 60a, and the lower end of the lateral extension 6b is designated by the reference sign 60b.

Figure 9F:
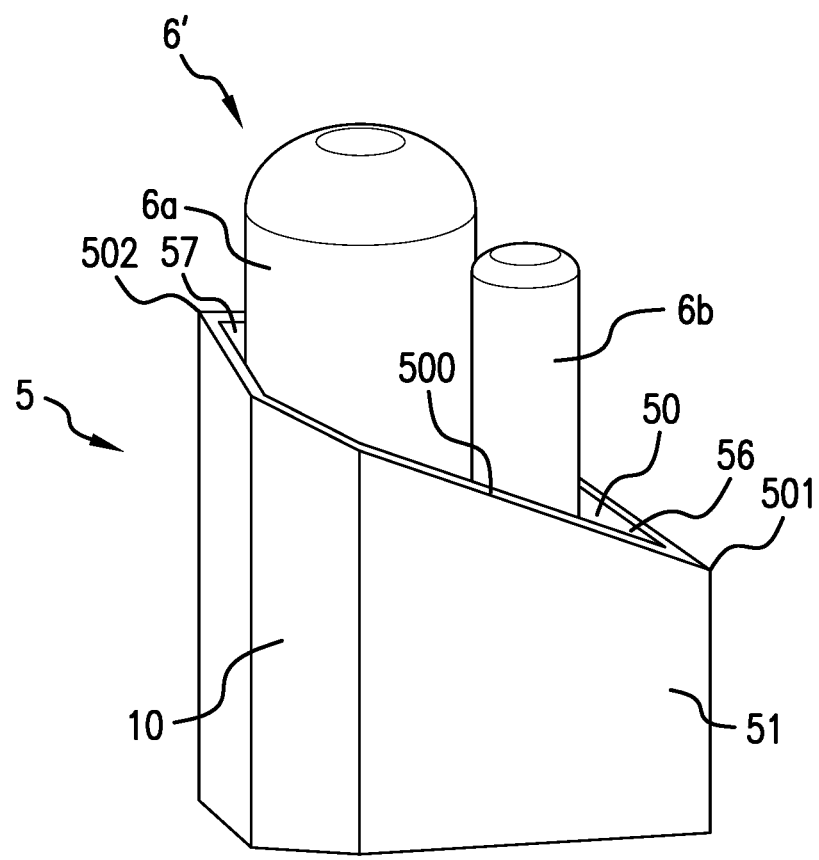
FIG. 9F illustrates the container having the lateral extension in a receptacle of the holding structure of FIGS. 9A to 9E when said container is finally held in the receptacle.
Figure 9H:
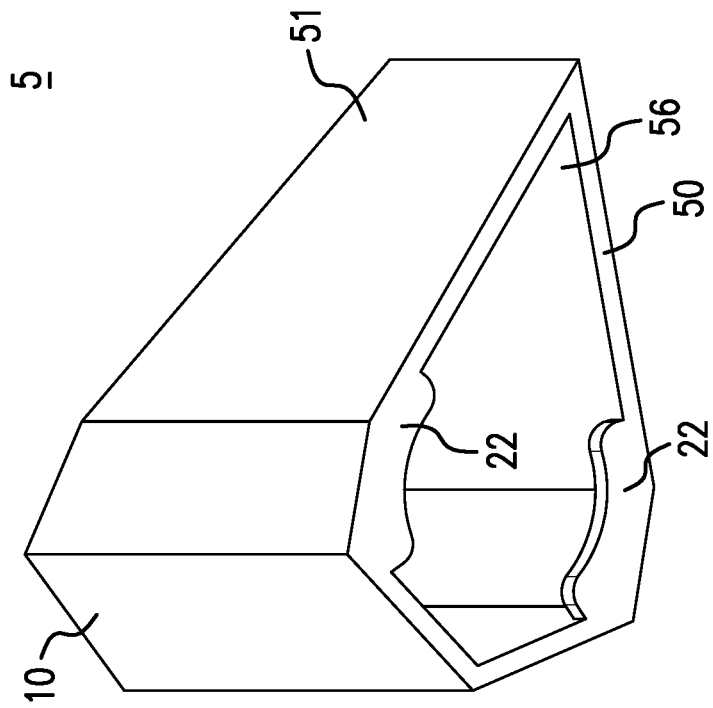
FIG. 9H illustrates the receptacle of FIGS. 9A to 9G in a perspective view from below.
Figure 9G:
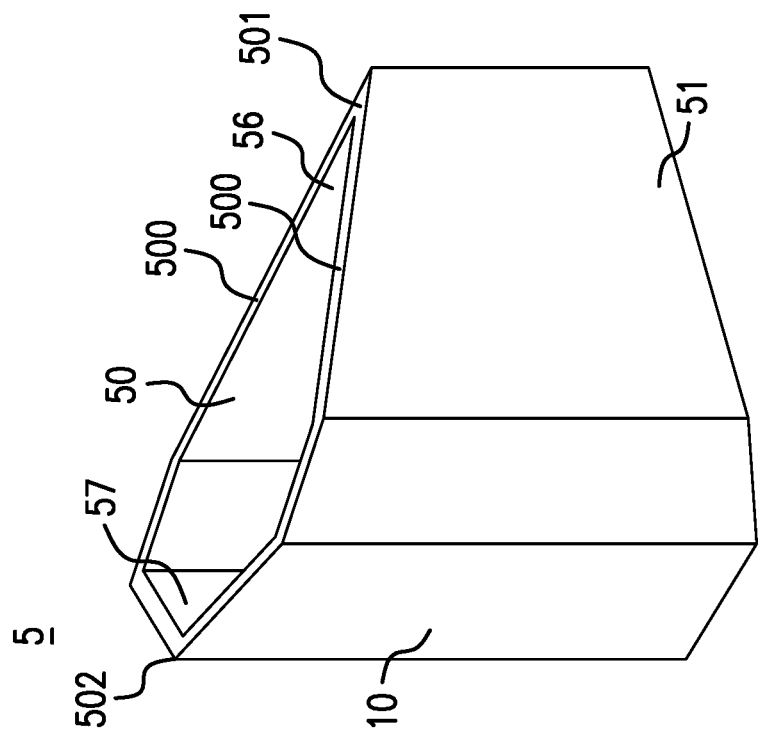
FIG. 9G illustrates the receptacle of FIGS. 9A to 9F in a perspective plan view.

The general geometry of the receptacles 5 is illustrated in FIGS. 9I and 9H and has already been described above with reference to FIG. 1E. The peripherally formed side wall 10 of the receptacle has two side wall portions 50, 51 which converge and form the widened clearance 56, wherein the illustrated small clearance 57 is formed at the opposite end of the receptacle by side wall portions. These two clearances 56, 57 arise when the device 6' is finally inserted into the receptacle, as illustrated in FIG. 9F. According to FIG. 9G, the upper edge of the peripherally formed side wall 10 is of bevelled design, with a local maximum 502 in the axial direction of the receptacle or in a direction perpendicular to the non-illustrated carrier (cf. FIG. 2A), and with a local minimum 501 as viewed in the same direction. A bevel 500 is formed between the maximum 502 or upper apex and the minimum 501 or lower apex on the upper edge of the side wall 10 and extends in a continuously inclined manner in the direction of the minimum 501 or lower apex.

As can be gathered from FIG. 9H, two holding projections 22 for supporting the lower end 60a of the main body 6a are provided on the lower end of the side wall 10, in the manner as described above with reference to FIG. 3B. These holding projections 22 are situated on the side of the receptacle 5 that is situated opposite to the widened clearance 56.

The basic shape of the receptacle 5 is tailored to the basic shape of the device 6' in such a way that the latter can be received therein, wherein in the held state, as illustrated in FIG. 9F, the lateral extension 6b is received in the widened clearance 56 and the main body 6a is received on the side of the receptacle that faces away from this clearance 56. The device 6' can be held exclusively by the holding projections illustrated in FIG. 9H. In principle, it is alternatively also possible, however, for other or additional holding elements to be provided, in particular holding projections in the region of the widened clearance for supporting the lower end of the lateral extension 6b.

In principle, for insertion, the device 6' should be oriented vertically from above into the receptacle 5 in such a way that the lateral extension 6b is aligned with the widened clearance 56. The device 6' can then be inserted without problem. Insertion bevels (not illustrated) on the upper edge of the side wall 10 can smoothly guide the device 6' here and ensure suitable centring of the device 6' in the receptacle 5.

However, such an optimum orientation of the device 6' cannot always be ensured. Thus, inaccuracies can occur, which make insertion vertically from above into the receptacle 5 more difficult, when such devices 6' having a non-cylindrical basic shape are handled by robots, gripping arms or the like.

If, then, a device 6' which is not perfectly oriented is inserted vertically from above into the receptacle 5, first of all the lower end 60a of the main body 6a and/or the lower end 60b of the lateral extension 6b come or comes into contact with the upper edge of the side wall 10, as illustrated in FIG. 9B. Assuming that the incorrect orientation of the device 6' does not differ all that much from the perfect orientation according to FIG. 9F, the lower end 60b of the lateral extension 6b then slides, following gravitational force, in the direction of the widened clearance 56, which leads to a change of certain rotation of the device 6' about its longitudinal axis until finally an optimum orientation according to FIG. 9F is achieved. For this purpose, it is conducive if, during insertion into the receptacle 5 vertically from above, the device 6' is held in a non-rotationally rigid manner and the robot, gripping arm or the like allows or actively drives a certain rotation of the device 6' about its longitudinal axis.

By virtue of the bevel 500 on the upper edge of the side wall 10, the lower end 60b of the lateral extension 6b finally slides, following gravitational force, further in the direction of the minimum 501 in the convergence region of the side wall portions 50, 51, as illustrated in the sequence of FIGS. 9C to 9E. Here, the main body 6a also engages ever further in the receptacle 5 until finally the state according to FIG. 9F is reached. In this state, the lateral extension 6b engages to its maximum in the widened clearance 56.

As described above, for inserting the device 6' into the receptacle 5, it is conducive for the device 6' to be held on the robot, gripping arm or the like in a non-rotationally rigid manner. Alternatively, the robot, gripping arm or the like allows a certain rotation of the device 6' about its longitudinal axis in order to allow a suitable orientation of the lateral extension 6b with the widened clearance 56.

In order to guide the lateral extension 6b, the bevel 500 does not necessarily have to extend over the entire upper edge of the side wall 10, in particular not entirely down to the lower apex 501 of the bevel 500. Rather, it may be sufficient if the bevel 500 is formed in certain portions at suitable positions of the upper edge of the side wall 10.

The aforementioned principle of guiding the lateral extension towards a widened clearance can also be applied to comparable devices or containers which have a plurality of lateral extensions, provided that the receptacles have a corresponding number of widened clearances for receiving these lateral extensions. Thus, for example, a device provided according to an exemplary embodiment can have two lateral extensions which project laterally from the main body on diametrically opposite sides thereof. In such a case, the receptacles would then be formed with two widened clearances, wherein two local maxima and two local minima are then formed on the upper edge of the peripherally formed side wall, between which maxima and minima bevels for guiding lower ends of device portions in the manner described above are provided, in order to ensure that the lateral extensions are oriented with the widened clearances during insertion of such a device into the receptacle.

A holding structure 1, as described above, can serve for storing and for transporting pharmaceutical containers, such as, for example, vials or carpoules. For handling, the holding structure 1 can be gripped and guided by gripping tools or the like by the access openings 9. The pharmaceutical containers can be further processed or treated while they are held by the holding structure 1, as described above. For sterile transport, such a holding structure can be stored as a so-called nest in a trough-shaped transport or packaging container (so-called tub), for instance in the manner as described above with reference to FIG. 3C. The transport or packaging container can be closed or sealed by a gas-permeable plastic film, in particular by a plastic film which is formed from a gas-permeable braid of plastic fibers and is in particular a Tyvek® film.

In some embodiments, a holding structure 1, as described above, can serve for storing and for transporting pharmaceutical containers, such as, for example, vials or carpoules. For handling, the holding structure 1 can be gripped and guided by gripping tools or the like by the access openings 9. The pharmaceutical containers can be further processed or treated while they are held by the holding structure 1, as described above. For sterile transport, such a holding structure can be stored as a so-called nest in a trough-shaped transport or packaging container (so-called tub), for instance in the manner as described above with reference to FIG. 3C. The transport or packaging container can be closed or sealed by a gas-permeable plastic film, in particular by a plastic film which is formed from a gas-permeable braid of plastic fibers such as a plastic film formed from high-density polyethylene fibers, and is in particular a Tyvek® film.

For sterile transport, such a transport or packaging container, where appropriate together with further transport or packaging containers of identical type, can be received in at least one sterile outer packaging bag and be packaged in a sterile manner with respect to the surroundings. The at least one sterile outer packaging bag can have a gas-permeable portion or even be formed completely thereof, which portion is formed in particular by a braid of plastic fibers, such as, for example, polypropylene fibers (PP).

As stated above, the design of the holding structure is optimized in particular with respect to the achievable packing density. In the solution according to the present invention, the in each case adjacent walls of the receptacles are combined to form a wall used commonly by two adjacent receptacles. Thin-walled, easily breakable rib-like contours which are difficult to cool in the tool design can thus be avoided according to the present invention, resulting in a longer service life of the tool. Furthermore, the cycle time of the production process can be significantly shortened and unit costs can be reduced.

The conventionally round geometry of receptacles is converted, according to the present invention, for relatively small volumes of the containers (for example up to 15 ml) into a hexagonal or diamond-shaped structure and for even greater volumes of the containers (for example of greater than 15 ml) into an octagonal structure, in which a 45° and 90° arrangement of the receptacles is possible. A very high packing density can thus be achieved. At the same time, the design of the tool for production by injection molding from a plastic is significantly simplified. Cooling of the molds and of the material can be realized in a very simple manner, and the cores of the molds can be produced in a simple and also standardized manner.

Furthermore, the design of the holding structure also with regard to stiffness and lightweight construction is optimized. In particular, the honeycomb design with side walls which are used commonly by adjacent receptacles and which are formed in one piece offers considerable advantages as regards the requirements placed on bending (bending of max. 2 mm with respect to the total area of the holding surface and measured in the empty state was able to be realized with problem).

The angular design of the receptacles in combination with the guide ribs simultaneously allows good accessibility for steam sterilization (for example by ETO in an autoclave).

A horizontal (flat) mold parting additionally has a very advantageous effect on the parting forces during demolding of the holding structure and thus on the risk of the formation of disturbing ridges and thus potential particles as a result of mold wear. In addition, the mold parting no longer takes place in the direct region of the holding structure itself.

By virtue of the optimized position of the mold parting plane, a holding structure provided according to the present invention has proved in particular to be completely suitable for clean room conditions because the risk of the creation of particles during demolding of the holding structure, but also during subsequent use, can be significantly reduced.

A holding structure within the sense of the present invention can be formed in one piece in particular by injection molding from a plastic. Also conceivable, in principle, is the production by 3D printing from a plastic. Thus, a further aspect of the present invention relates to a computer- or processor-readable file, also for transmission via networks, such as, for example, an in-house computer network or via the Internet, comprising instructions or control commands which, if these are loaded by a computer or a processor, have the effect that a 3D printer under control by the computer or processor prints a holding structure, as disclosed in the present application, from a suitable material, in particular from a plastic material, in three-dimensional form.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE SIGNS

1 Holding structure
2 Plate-shaped carrier
4 Rounded-off corner region
5 Receptacle (of polygonal design)
5 Receptacle
6 Receptacle
6 Container
6' Medical device
6a Main body
60a Lower end of main body 6a
6b Lateral extension of main body 6a
60b Lower end of lateral extension 6b
9 Access opening
10 Side wall 10a Side wall portion above carrier 2
10b Side wall portion below carrier 2
18 Guide and positioning rib
19 Insertion bevel of guide and positioning rib 18
20 Further guide and positioning rib
22 Holding projection
25 Opening
40 Central connecting portion
41 Upper edge of central connecting portion
42 Opening
43 Cavity
50 First side wall
50b First side wall
51 Second side wall
51a, 51b Second side wall
52 Apex region at point with smallest transverse dimension of receptacle 5
52a Local maximum
52b Local minimum
53 Axis of symmetry
53a, 53b Axis of symmetry
54 Convergence region
54a, 54b Convergence region
55 Connecting web
56 Widened clearance for handling
56a, 56b Widened clearance for handling
57 Small clearance
58 Convergence region of small clearance 57
58a, 58b Convergence region of small clearance 57a or 57b
500 Bevel
501 Minimum
502 Maximum
60 Carpoule/Container
60' Carpoule in lifted position
61 Vial/Container
62 Cylindrical side wall
63 Bottom
64 Shoulder portion
65 Narrowed neck portion
66 Upper edge
67 Filling opening
68 Ejection opening
69 Syringe body
70 Flange of syringe body 69
80 Tool for handling
81 Handling arm
82 Front end of handling arm 81
83 Recess
90 Transport and packaging container
91 Bottom of transport and packaging container 90
92 Lower side wall of transport and packaging container 90
93 Step
94 Upper side wall of transport and packaging container 90
95 Flange at the upper end of upper side wall 94
α Convergence angle
M Geometric center of receptacle 5 or received container

RE THE PRIOR ART

100 Holding structure
101 Receptacle
102 Container with circular outer contour
103 Side wall
104 Clearance
105 First side wall of pair of side walls 103 which converge in a common corner point
106 Second side wall of pair of side walls 103 which converge in a common corner point
M' Geometric center of receptacle 101
MS Mid-perpendicular
Θ Angle at which first side wall 105 and second side wall 106 converge

What is claimed is:

1. A device for simultaneously holding a plurality of containers for substances for pharmaceutical, medical or cosmetic applications or of devices having such containers, the device comprising:
a holding structure, which is the device and includes a plurality of receptacles configured to each receive a respective one of the containers or devices, the receptacles being arranged in a regular arrangement and formed by peripherally formed side walls, the receptacles being configured to tailor to an outer contour of the containers or devices in such a way that an annular gap is formed between a side wall of one of the containers or devices and a respective one of the peripherally formed side walls of a respective one of the receptacles when the containers or devices are received in the receptacles, the receptacles, as viewed in a plan view, starting from an imaginary basic shape that is point-symmetrical or mirror-symmetrical, being compressed in a first direction and expanded in a second direction transversely to the first direction, with the result that the gap in at least one region of the receptacles is widened to form a widened clearance for handling containers or devices which are received in the receptacles, the holding structure further including an upper side, the peripherally formed side walls including an upper edge which forms a closed, smooth curve having at least one local maximum and at least one local minimum in a direction perpendicular to the upper side of the holding structure, the at least one local minimum being situated in a region of the widened clearance that is respectively assigned.

2. The device of claim 1, wherein the holding structure includes a plate-shaped carrier which forms the upper side of the holding structure, wherein the peripherally formed side walls and the receptacles project perpendicularly from the plate-shaped carrier.

3. The device of claim 2, wherein the upper edge of the peripherally formed side walls forms a slide or an inclined ramp, the slide or inclined ramp being configured for allowing an angular orientation of the containers or devices having an asymmetrical basic shape.

4. The device of claim 3, wherein the slide or inclined ramp is configured such that the containers—which are wider in a third direction than in a direction perpendicular thereto—are, during an insertion into the receptacles, guided automatically vertically from above and rotated in such a way that the third direction in which the containers or devices are wider is automatically oriented parallel to a direction of the receptacles in which the receptacles are wider, which allows for an automatic angle of rotation orientation of the containers or devices.

5. The device of claim 3, wherein a respective one of the receptacles includes two of the widened clearance which oppose one another, the at least one local minimum being at least one first local minimum, the closed, smooth curve including at least one second local minimum which is positioned between the two of the widened clearance.

6. The device of claim 3, wherein the closed, smooth curve includes a concave portion and is configured for facilitating an insertion of the containers or devices from vertically above the holding structure into the receptacles.

7. The device of claim 6, wherein the at least one local maximum is positioned a distance from the upper side that is farther than a distance from the upper side of a remainder of the peripherally formed side walls.

8. The device of claim 7, wherein the closed, smooth curve—with the at least one local maximum and the at least one local minimum—forms a stacking feature configured for facilitating a space-saving stacking of a plurality of the holding structure vertically relative to one another.

9. The device of claim 8, wherein the stacking feature is configured for facilitating the space-saving stacking because an undesired jamming of the upper edge of the peripherally formed side walls is avoided.

10. The device of claim 1, wherein the gap in the at least one region of the receptacles is configured for being widened to form the widened clearance for allowing an access by at least one tool to, and thereby for handling, containers or devices which are received in the receptacles.

11. The device of claim 1, wherein a convergence angle associated with two of the side walls of the receptacle forming the widened clearance is an acute angle.

12. The device of claim 1, wherein guide ribs, which extend in a longitudinal direction of the receptacles, are formed on the side walls.

* * * * *